United States Patent
Kushibiki et al.

(10) Patent No.: US 6,691,575 B2
(45) Date of Patent: Feb. 17, 2004

(54) MATERIAL EVALUATION METHOD BY ACOUSTIC VELOCITY MEASUREMENT

(75) Inventors: Jun-ichi Kushibiki, 2-71, Yamada-honcho, Taihaku-ku, Sendai-shi, Miyagi (JP), 982-0816; Izumi Watanabe, Miyagi (JP); Yuji Ohashi, Miyagi (JP)

(73) Assignee: Jun-Ichi Kushibiki, Miyagi (JP)

( * ) Notice: Subject to any disclaimer, the term of this patent is extended or adjusted under 35 U.S.C. 154(b) by 15 days.

(21) Appl. No.: 10/093,625

(22) Filed: Mar. 8, 2002

(65) Prior Publication Data

US 2002/0124651 A1 Sep. 12, 2002

(30) Foreign Application Priority Data

Mar. 12, 2001 (JP) ........................................ 2001-069181

(51) Int. Cl.[7] ........................... G01H 5/00; G01K 11/00; G01N 24/00; G01N 29/02; G01N 29/04
(52) U.S. Cl. ............................. 73/597; 73/598; 73/600; 73/602
(58) Field of Search ........................ 73/597, 590, 602, 73/629, 25.01, 56.01; 367/140, 150

(56) References Cited

U.S. PATENT DOCUMENTS

| | | | | |
|---|---|---|---|---|
| 5,295,487 A | * | 3/1994 | Saitoh et al. | 600/459 |
| 5,351,219 A | * | 9/1994 | Adachi et al. | 367/140 |
| 6,131,257 A | * | 10/2000 | Nishihara et al. | 29/25.35 |
| 6,250,137 B1 | * | 6/2001 | Takahashi et al. | 73/64.53 |

OTHER PUBLICATIONS

Kushibiki J, Ohashi Y., Ono Y., "Evaluation and selection of LiNbO3 and LiTaO3 substrates for SAW Devices by the LFB ultrasonic material characterization method" IEEE Transactions on Ultrasonics, Ferroelectronics and Frequency Control, vol. 47, No. 4, Jul. 2000, pp. 1068–1076.

J. Kushibiki and N. Chubachi, "Material characterization by line–focus–beam acoustic microscope," IEEE Trans. Sonics and Ultrason., vol. SU–32, pp. 189–212 (1985).

M. Sato, A Iwama, J. Yamada, M. Hikita, and Y. Furukawa, "SAW velocity variation of LiTaO3 substrates," Jpn. J. Appl. Phys., vol. 28, Suppl. 28–1, pp. 111–113 (1989).

K. Yamada, H. Takemura, Y. Inoue, T. Omi, and S. Matsumura, "Effect of Li/Nb ratio on the SAW velocity of 128° Y–X LiNbO3 wafers," Jpn. Appl. Phys., vol. 26, Suppl. 26–2, pp. 219–222 (1987).

J. Kushibiki, I. Takanaga, M. Arakawa, and T. Sannomiya, "Accurate measurements of the acoustical physical constants of LiNbO3 and LiTaO3 single crystals," IEEE Trans. Ultrson., Ferroelect., Freq. Contr., vol. 46, pp. 1315–1323 (1999).

I. Takanaga and J. Kusibiki, "A method of determining acoustical physical constants for piezoelectric materials by line–focus–beam acoustic microscopy," 20th Ultrason. Symp. Proc., pp. 125–126 (1999).

I. Takanaga and J. Kusibiki, "A method of determining acoustical physical constants for piezoelectric materials by line–focus–beam acoustic microscopy," Technical Report of IEICE, US99–38, pp. 9–16 (1999).

(List continued on next page.)

Primary Examiner—Hezron Williama
Assistant Examiner—Jacques Saint-Surin
(74) Attorney, Agent, or Firm—David N. Lathrop, Esq.; Gallagher & Lathrop

(57) ABSTRACT

All independent acoustical physical constants (elastic constants, piezoelectric constants, dielectric constants and density) of a material are predetermined as a function of its chemical composition, and the calibration line between the acoustic velocity for each of the substrate crystal plane, the propagation direction and the propagation mode, and other chemical and physical properties is numerically calculated with ease without making any experiments.

16 Claims, 25 Drawing Sheets

OTHER PUBLICATIONS

J. Kushibiki, T. Okuzawa, J. Hirohashi, and Y. Ohashi, "Line–focus–beam acoustic microscopy characterization of optical–grade LiTaO3 single crystals," J. Appl. Phys., vol. 87, pp. 4395–4403 (2000).

J. J. Campbell and W. R. Jones, "Propagation of surface waves at the boundary between a piezoelectric crystal and a fluid medium," IEEE Trans. Sonics and Ultrason., vol. SU–17, pp. 71–76 (1970).

J. J. Campbell and W. R. Jones, "A method for estimating optimal crystal cuts and propagation directions for excitation of piezoelectric surface waves," IEEE Trans. Sonics and Ultrason., vol. SU–15, pp. 209–217 (1968).

K. Yamada, T. Omi, S. Matsumura, and T. Nishimura, "Characterization of 4–inch LiTaO3 single crystals for SAW device application," IEEE Ultrason. Symp. Proc., pp. 243–248 (1984).

* cited by examiner

FIG. 1

TABLE 1

|  | STARTING MATERIAL $Li_2O$ CONTENT [mol%] | CURIE TEMP MEASURED VALUE [°C] | GROWN CRYSTAL $Li_2O$ CONTENT [mol%] |
|---|---|---|---|
| $LiTaO_3$ | 48.0 | 595.81 | 48.350 |
| | 48.5 | 601.75 | 48.504 |
| | 49.0 | 607.66 | 48.656 |
| $LiNbO_3$ | 48.0 | 1124.1 | 48.278 |
| | 48.5 | 1130.0 | 48.410 |
| | 49.0 | 1136.2 | 48.548 |

FIG. 11

TABLE 2

| | | 48.350 mol% | 48.504 mol% | 48.656 mol% | GRAD (/mol%) |
|---|---|---|---|---|---|
| ELASTIC CONSTANT ($\times 10^{11}$ N/m$^2$) | $c_{11}^E$ | 2.3264 | 2.3300 | 2.3333 | 0.022 |
| | $c_{12}^E$ | 0.4620 | 0.4643 | 0.4653 | 0.011 |
| | $c_{13}^E$ | 0.8356 | 0.8341 | 0.8358 | 0.000 |
| | $c_{14}^E$ | -0.1077 | -0.1061 | -0.1054 | 0.008 |
| | $c_{33}^E$ | 2.7530 | 2.7574 | 2.7614 | 0.027 |
| | $c_{44}^E$ | 0.9513 | 0.9514 | 0.9521 | 0.002 |
| PIEZO-ELECTRIC CONSTANT (C/m$^2$) | $e_{15}$ | 2.609 | 2.634 | 2.650 | 0.132 |
| | $e_{22}$ | 1.818 | 1.826 | 1.844 | 0.084 |
| | $e_{31}$ | -0.143 | -0.090 | -0.114 | 0.094 |
| | $e_{33}$ | 1.804 | 1.792 | 1.779 | -0.080 |
| DIELECTRIC CONSTANT | $\varepsilon_{11}^S/\varepsilon_0$ | 41.71 | 41.69 | 41.71 | 0.00 |
| | $\varepsilon_{33}^S/\varepsilon_0$ | 41.92 | 41.73 | 41.40 | -1.70 |
| DENSITY (kg/m$^3$) | $\rho$ | 7463.44 | 7460.56 | 7457.85 | -18.26 |

FIG. 12

TABLE 3

| | | 48.278 mol% | 48.410 mol% | 48.548 mol% | GRAD (/mol%) |
|---|---|---|---|---|---|
| ELASTIC CONSTANT ($\times 10^{11}$ N/m$^2$) | $c_{11}^E$ | 1.9844 | 1.9883 | 1.9916 | 0.027 |
| | $c_{12}^E$ | 0.5433 | 0.5463 | 0.5489 | 0.021 |
| | $c_{13}^E$ | 0.6794 | 0.6811 | 0.6820 | 0.010 |
| | $c_{14}^E$ | 0.0758 | 0.0779 | 0.0799 | 0.015 |
| | $c_{33}^E$ | 2.3382 | 2.3431 | 2.3459 | 0.028 |
| | $c_{44}^E$ | 0.5996 | 0.5984 | 0.5973 | -0.008 |
| PIEZO-ELECTRIC CONSTANT (C/m$^2$) | $e_{15}$ | 3.631 | 3.659 | 3.682 | 0.191 |
| | $e_{22}$ | 2.394 | 2.408 | 2.419 | 0.093 |
| | $e_{31}$ | 0.332 | 0.328 | 0.320 | -0.045 |
| | $e_{33}$ | 1.896 | 1.878 | 1.870 | -0.094 |
| DIELECTRIC CONSTANT | $\varepsilon_{11}^S/\varepsilon_0$ | 45.11 | 45.08 | 45.04 | -0.26 |
| | $\varepsilon_{33}^S/\varepsilon_0$ | 26.81 | 26.64 | 26.45 | -1.33 |
| DENSITY(kg/m$^3$) | $\rho$ | 4643.54 | 4642.76 | 4641.67 | -6.94 |

FIG. 15

TABLE 4

| PROPAGATION MODE AND DIRECTION | SPECIMEN CUTTING POSITION | MEASURED VALUE | DIFFERENCE FROM TOP-SECTION SUBSTRATE | ESTIMATED AMOUNT OF CHANGE IN $Li_2O$ CONCENTRATION (mol%) |
|---|---|---|---|---|
| LONGITUDINAL WAVE VELOCITY PROPAGATING IN Y-AXIS DIRECTION (m/s) | TOP | 5746.2 | — | — |
| | MIDDLE | 5746.4 | +0.2 | +0.004 |
| | BOTTOM | 5747.1 | +0.9 | +0.020 |
| LSAW VELOCITY PROPAGATING IN Y-CUT Z-AXIS DIRECTION (m/s) | TOP | 3228.6 | — | — |
| | MIDDLE | 3228.7 | +0.1 | +0.006 |
| | BOTTOM | 3229.0 | +0.4 | +0.023 |

FIG. 19

TABLE 5

| | LSAW VELOCITY | LATTICE CONSTANT $a$ | CURIE TEMP | Li$_2$O CONCENTRATION | SAW VELOCITY |
|---|---|---|---|---|---|
| LSAW VELOCITY | — | $-6.07 \times 10^{-5}$ [Å/(LSAW-m/s)] | 1.70 [°C/(LSAW-m/s)] | 0.0439 [mol%/(LSAW-m/s)] | 1.85 [(SAW-m/s)/(LSAW-m/s)] |
| LATTICE CONSTANT $a$ | $-0.165 \times 10^5$ [(LSAW-m/s)/Å] | — | $-0.280 \times 10^5$ [°C/Å] | $-0.00723 \times 10^5$ [mol%/Å] | $-0.305 \times 10^5$ [(SAW-m/s)/Å] |
| CURIE TEMP | 0.588 [(LSAW-m/s)/°C] | $-3.57 \times 10^{-5}$ [Å/°C] | — | 0.0258 [mol%/°C] | 1.09 [(saw-m/s)/°C] |
| Li$_2$O CONCENTRATION | 22.8 [(LSAW-m/s)/mol%] | $-138 \times 10^{-5}$ [Å/mol%] | 38.7 [°C/mol%] | — | 42.4 [(SAW-m/s)/mol%] |
| SAW VELOCITY | 0.540 [(LSAW-m/s)/(SAW-m/s)] | $-3.28 \times 10^{-5}$ [Å/(SAW-m/s)] | 0.919 [°C/(saw-m/s)] | 0.0237 [mol%/(SAW-m/s)] | — |

FIG. 20

TABLE 6

| | | LSAW VELOCITY [m/s] | LATTICE CONSTANT a [×10⁻⁵ Å] | CURIE TEMP [°C] | Li₂O CONCENTRATION [mol%] | SAW VELOCITY [m/s] |
|---|---|---|---|---|---|---|
| DISTRIBUTION IN WAFER SURFACE | A | 0.13~0.25 | 0.80~1.51 | 0.22~0.42 | 0.006~0.011 | 0.24~0.46 |
| | B | 0.13~0.18 | 0.80~1.09 | 0.22~0.30 | 0.006~0.008 | 0.23~0.33 |
| DISTRIBUTION IN INGOT | A | 0.52~0.96 | 3.16~5.83 | 0.88~1.63 | 0.023~0.042 | 0.96~1.77 |
| | B | 0.59~0.61 | 3.58~3.70 | 1.00~1.04 | 0.026~0.027 | 1.09~1.14 |
| DISTRIBUTION AMONG WAFERS | A | 2.00 | 12.15 | 3.40 | 0.088 | 3.70 |
| | B | 1.30 | 7.89 | 2.21 | 0.057 | 2.41 |

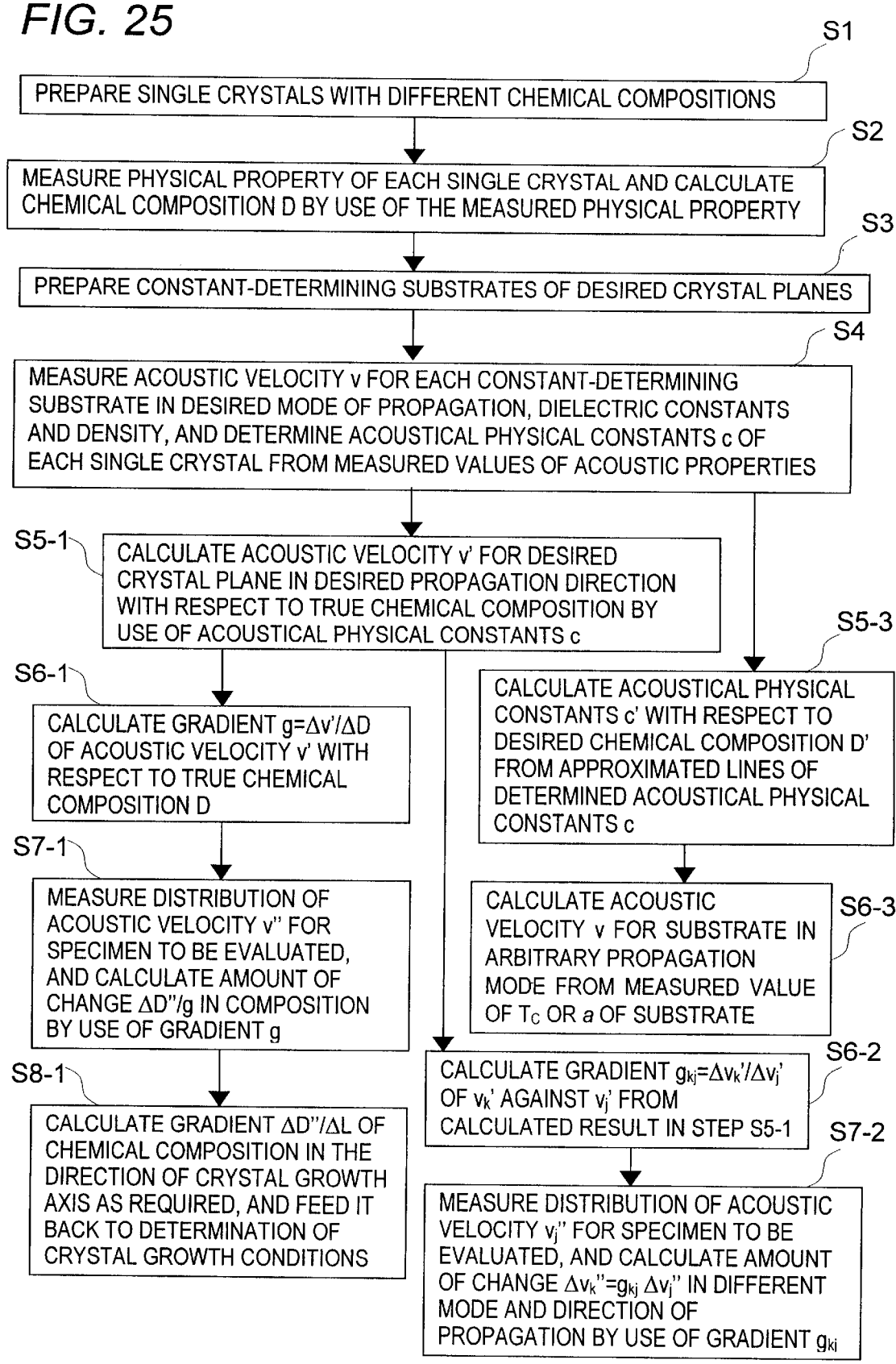

MATERIAL EVALUATION METHOD BY ACOUSTIC VELOCITY MEASUREMENT

BACKGROUND OF THE INVENTION

The present invention relates to a method for efficient evaluation of various materials and determination/improvement of the conditions for their production, using measured values of the phase velocity (hereinafter referred to simply as velocity) of surface or bulk acoustic waves.

Under present circumstances, the evaluation of materials (crystals, in particular) widely used in electronic device industries is made, in general, by use of the lattice constant measured by X-ray diffractometry and the Curie temperature by differential thermal analysis or the like. In particular, surface acoustic wave (SAW) device materials are mostly evaluated empirically using parameters (lattice constant and Curie temperature) in place of the velocities of acoustic waves.

At the laboratory level, it is common practice to evaluate materials by use of the phase velocities of leaky surface acoustic waves (LSAWs) measured by line-focus-beam (LFB) ultrasonic microscopy [Literature 1]. LSAW is an acoustic wave that propagates at the boundary between a fluid medium (water couplant) and the specimen surface, and its propagation characteristic is specific to every material. The main factor that dominates the homogeneity of crystals is the distribution of their chemical composition. A change in the chemical composition is detected as a change in the LSAW velocity to evaluate the crystals. In this case, the relationship (a calibration line) between the chemical composition and the LSAW velocity needs to be premeasured experimentally. This involves: the preparation of a specimen of the same cut plane as that of every substrate to be evaluated; measurements of the LSAW velocity in a particular propagation direction and the Curie temperature of the specimen by differential thermal analysis; and the determination of the above-mentioned relationship between the LSAW velocity and the chemical composition based on the measured values of the LSAW velocity and Curie temperature. This procedure is inefficient because it must be performed prior to the evaluation of each substrate for different crystal planes and different propagation directions.

In the case of SAW device materials, in particular, evaluation by the SAW velocity is a direct evaluation and hence is important or preferable from the practical point of view since the SAW devices utilize the propagation characteristics of SAWs that propagate on the substrate surface with no water loaded thereon (a free surface). Theoretically, however, LFB ultrasonic microscopy is limited specifically to the measurement of the SAW velocity in the propagation mode (Rayleigh type) in which to excite the SAWs on the water-loaded substrate surface; hence, it is difficult to directly measure the SAW velocity (especially, a shear horizontal wave (SH wave) type (hereinafter referred to simply as SH-type) SAW). At present, the SAW velocity could be measured, for example, by directly exciting SAWs on the substrate surface with electrodes formed thereon, but few material manufacturers adopt such a direct evaluation method.

In the material evaluation by LFB ultrasonic microscopy, the amount of change in the LSAW velocity due to a change in the chemical composition of the material differs for different substrate surfaces and different propagation directions, and a calibration line that represents the relationship between the chemical composition and the LSAW velocity must be prepared experimentally for each substrate and for each propagation direction; this is time-consuming and laborious. Further, in order that the change in the chemical composition detected as the LSAW velocity may be evaluated as the SAW velocity, it is necessary to experimentally obtain the relationship between the SAW and the LSAW velocity by measuring the SAW velocity for a substrate with electrodes formed on its surface, but this method is inefficient.

SUMMARY OF THE INVENTION

It is therefore an object of the present invention to provide a method for efficient material evaluation by preparing the calibration line of the acoustic velocity with respect to the chemical composition without the need for experimentally preparing it for all possible combinations of substrate crystal planes and directions and modes of propagation.

Another object of the present invention is to provide a material evaluation method that permits direct numerical calculation of the relationship of velocity between acoustic waves in various modes of propagation (for example, between the SAW and the LSAW and between longitudinal and shear waves) for an arbitrary chemical composition without involving any particular experimental procedures.

Still another object of the present invention is to provide a material evaluation method that allows efficient evaluation of acoustic characteristics, permitting direct evaluation of materials by use of the acoustic wave velocity measured therefor with high accuracy, in place of the Curie temperature and lattice constant.

According to the present invention, desired independent, acoustical physical constants of materials (elastic, piezoelectric and dielectric constants and density for a piezoelectric material, and elastic constants and density for a non-piezoelectric material) are predetermined as a function of the chemical composition. This enables numerical calculation of the acoustic velocity for a desired combination of the substrate cut plane and the direction and mode of propagation, permitting efficient evaluation of materials and determination/improvement of the conditions for their production by acoustic velocity measurements.

BRIEF DESCRIPTION OF THE DRAWINGS

FIG. 1 is a table showing measured values of Curie temperature of specimens cut from substantially middle sections of grown crystals and their $Li_2O$ contents converted from the measured values of Curie temperature;

FIG. 11 is a table showing acoustical physical constants of the LiTaO$_3$ single crystals;

FIG. 12 is a table showing acoustical physical constants of the LiNbO$_3$ single crystals;

FIG. 15 is a table showing examples of velocity variations in the LiTaO$_3$ single crystal estimated as variations in the chemical composition by use of the relationships between velocities in respective propagation modes and chemical compositions calculated from constants determined by the present invention;

FIG. 19 is a table showing the interrelationships among chemical and physical properties of the 42° YX-LiTaO$_3$ single crystals;

FIG. 20 is a table showing the distributions of chemical and physical properties converted from the LSAW distributions in the wafer surface, in an ingot and among different wafers of 42° YX-LiTaO$_3$ single crystals of Manufactures A and B;

FIG. 25 is a flowchart for explaining the single crystal material evaluation procedure according to the present invention.

DETAILED DESCRIPTION OF THE PREFERRED EMBODIMENTS

A description will be given first of ferroelectric LiTaO$_3$ and LiNbO$_3$ single crystals. In the first place, three LiTaO$_3$ single crystals and three LiNbO$_3$ single crystals, grown from starting materials having Li$_2$O contents of 48.0, 48.5 and 49.0 mol %, respectively, are prepared as crystals of largely different chemical compositions. The Curie temperature of a specimen cut from the middle portion of each crystal (ingot) is measured by the thermal analysis method, and the chemical composition of each crystal is determined using known relationships between measured values of the Curie temperature and chemical compositions ([Literature 2] for the LiTaO$_3$ single crystal and [Literature 3] for the LiNbO$_3$ single crystal). The measured values of the Curie temperature and chemical compositions thus determined are shown in Table 1 of FIG. 1.

Next, specimens for accurately determining acoustical physical constants are prepared from the above-mentioned single crystal ingots by use of methods described in

Figure 2A:
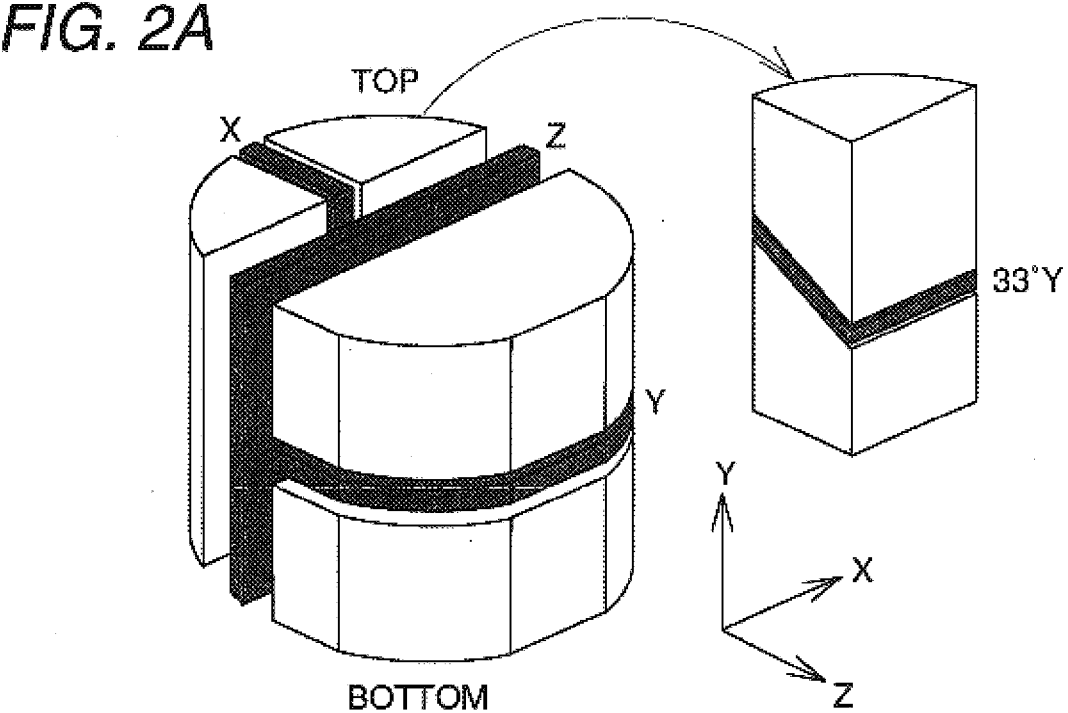
FIG. 2A is a diagram showing the sections of a $LiTaO_3$ single crystal ingot from which specimens are cut.
Figure 2B:
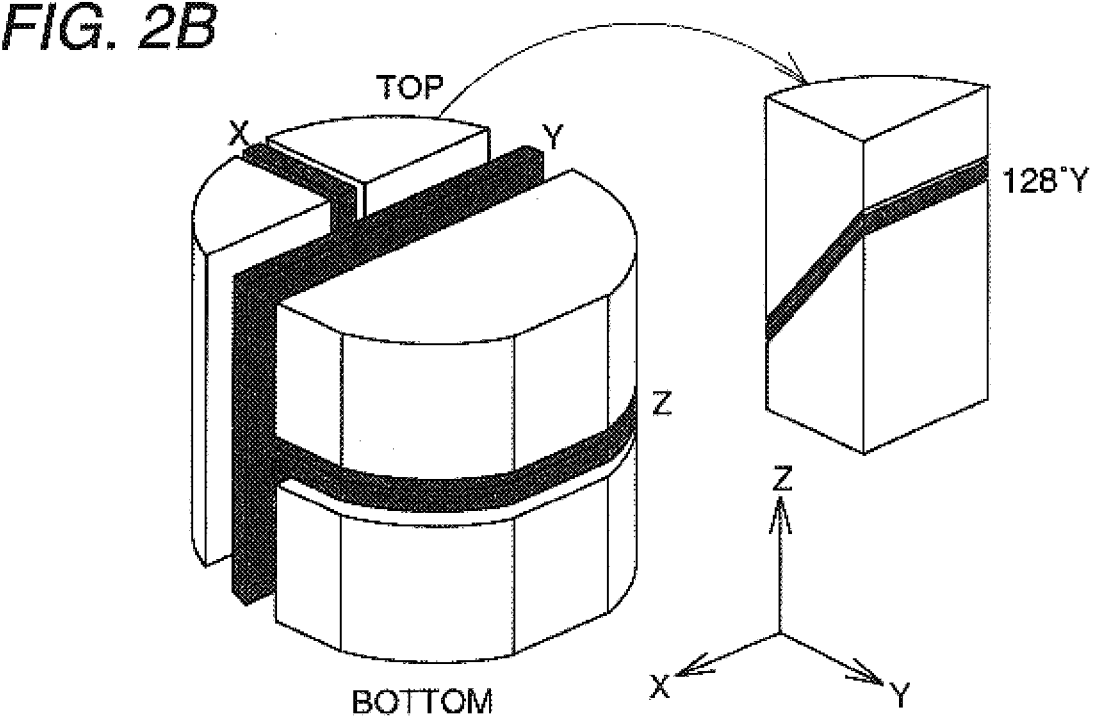
FIG. 2B is a diagram showing the sections of a $LiNbO_3$ single crystal ingot from which specimens are cut.

[Literature 4], [Literature 5], or [Literature 6]. FIG. 2 depicts, by way of example, how to prepare the specimens from the single crystal ingots. From each LiTaO$_3$ single crystal ingot are prepared a total of four substrates that have X-, Y- and Z-cut principal planes and a 32.93° rotated Y-cut (simply described as 33° Y-cut) plane, respectively, as shown in FIG. 2A. From each LiNbO$_3$ single crystal ingot are prepared a total of four substrates that have X-, Y- and Z-cut principal planes and a 127.85° rotated Y-cut (simply described as 128° Y-cut) plane, respectively, as shown in FIG. 2B. Each substrate is 3 to 4 mm thick and has its both sides optically polished.

In general, the composition of a crystal grown from a melt of a chemical composition deviating from a congruent composition monotonously changes (increases or decreases) in the lengthwise direction of the single crystal [Literature 7]. Accordingly, by preparing specimens that contain the direction of crystal growth axis like the Z-cut plate in FIG. 2A or Y-cut plate in FIG. 2B and the direction of diameter of the crystal like the Y-cut plate in FIG. 2A or Z-cut plate in FIG. 2B, the distribution of the chemical composition in the crystal can easily be detected as the velocity distribution. When the velocity is measured at a different position for each substrate, the amount of deviation of the chemical composition due to the difference in the position of measurement is estimated from the velocity distribution, and the estimated value can be used to correct the measured velocity value; hence, the above-mentioned constants can be determined with higher accuracy. Further, by premeasuring the difference between each substrate surface and the actual crystal plane by X-ray diffraction, the velocity-measured value of each substrate can be corrected using the premeasured value; hence, the constants can be determined with higher accuracy.

Figure 3A:
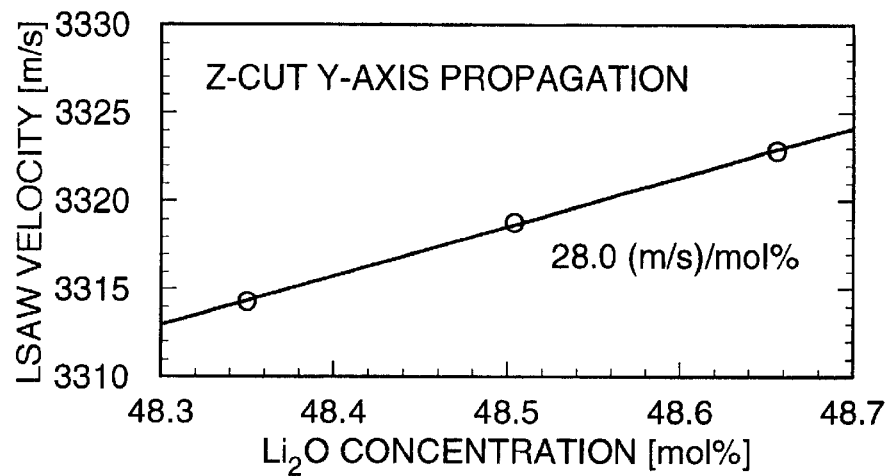
FIG. 3A is a graph showing measured values of the chemical composition dependence of Y-propagating LSAW velocities on Z-cut $LiTaO_3$ specimens.
Figure 3B:
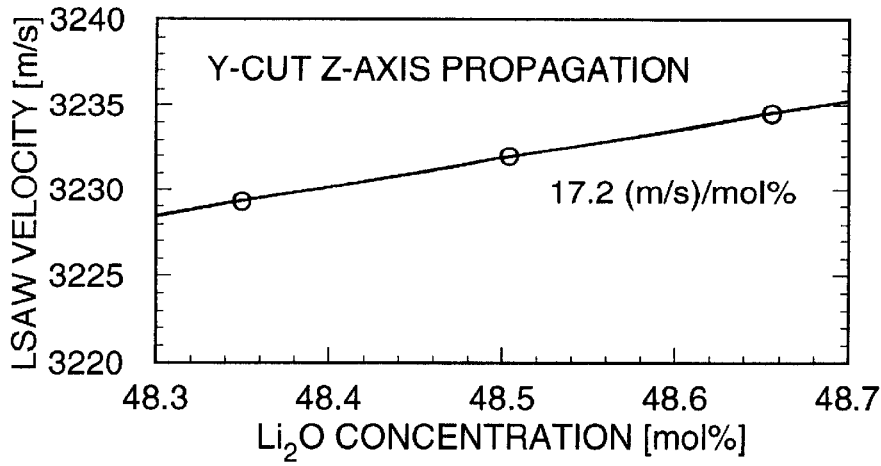
FIG. 3B is a graph showing measured values of the chemical composition dependence of Z-propagating LSAW velocities on Y-cut $LiTaO_3$ specimens.
Figure 3C:
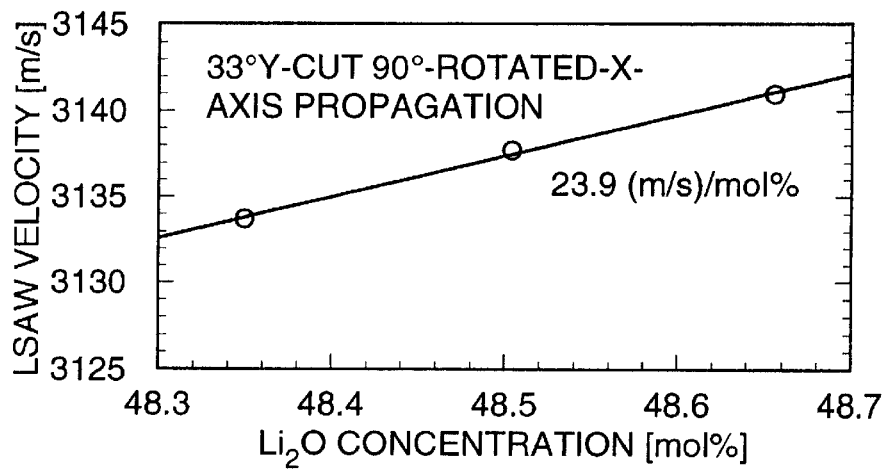
FIG. 3C is a graph showing measured values of the chemical composition dependence of 90° X-propagating LSAW velocities on 33° Y-cut $LiTaO_3$ specimens.
Figure 4A:
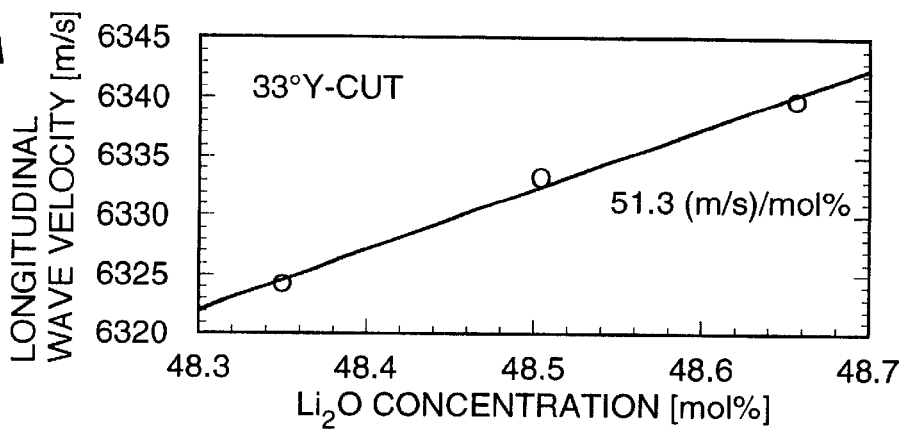
FIG. 4A is a graph showing measured values of the chemical composition dependence of longitudinal wave velocities in the 33° Y-cut $LiTaO_3$ specimens.
Figure 4B:
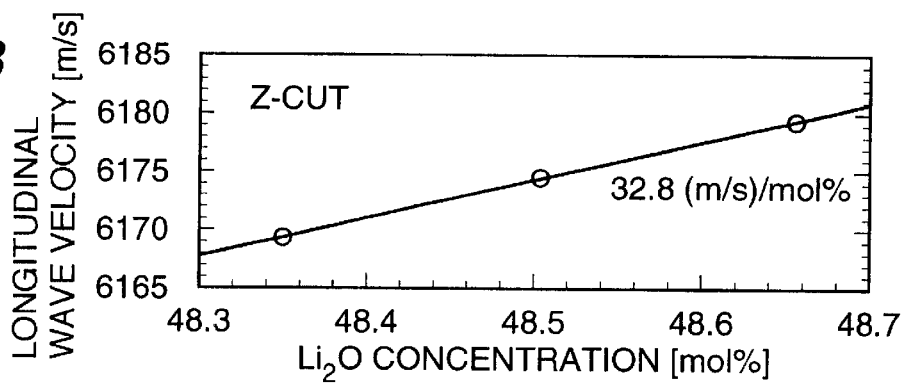
FIG. 4B is a graph showing measured values of the chemical composition dependence of longitudinal wave velocities in the Z-cut $LiTaO_3$ specimens.
Figure 4C:
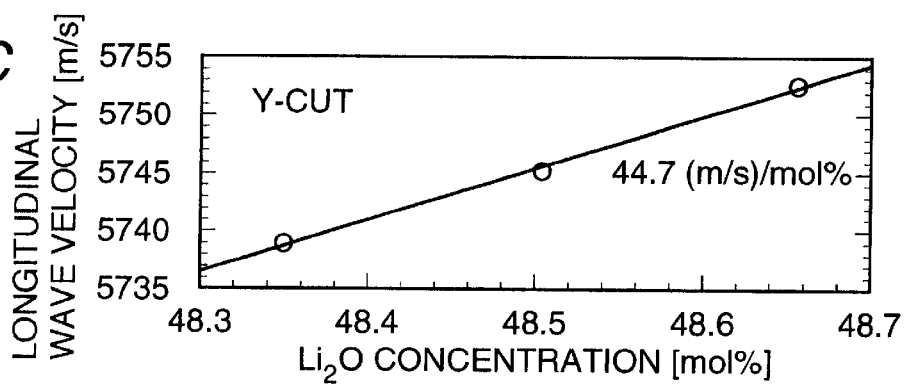
FIG. 4C is a graph showing measured values of the chemical composition dependence of longitudinal wave velocities in the Y-cut LiTaO$_3$ specimens.
Figure 4D:
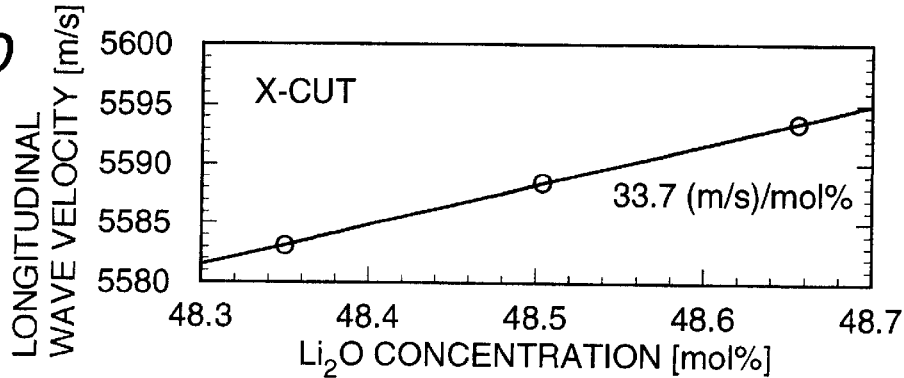
FIG. 4D is a graph showing measured values of the chemical composition dependence of longitudinal wave velocities in the X-cut LiTaO$_3$ specimens.
Figure 5A:
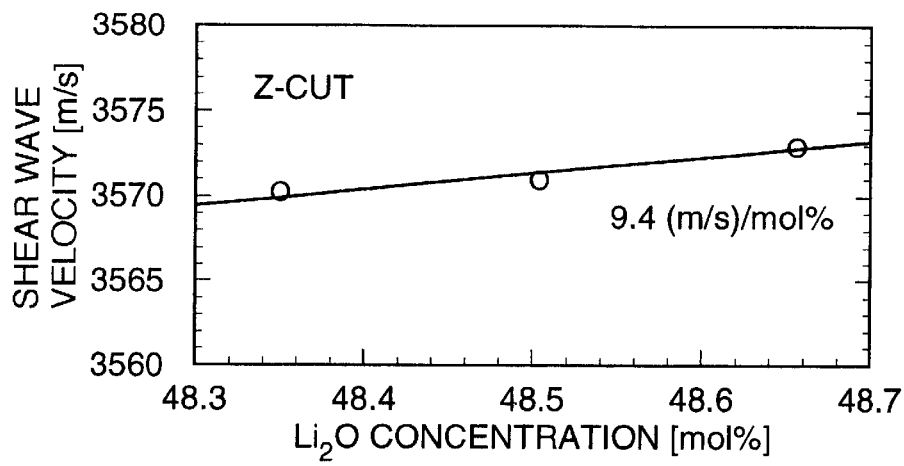
FIG. 5A is a graph showing measured values of the chemical composition dependence of shear wave velocities in the Z-cut LiTaO$_3$ specimens.
Figure 5B:
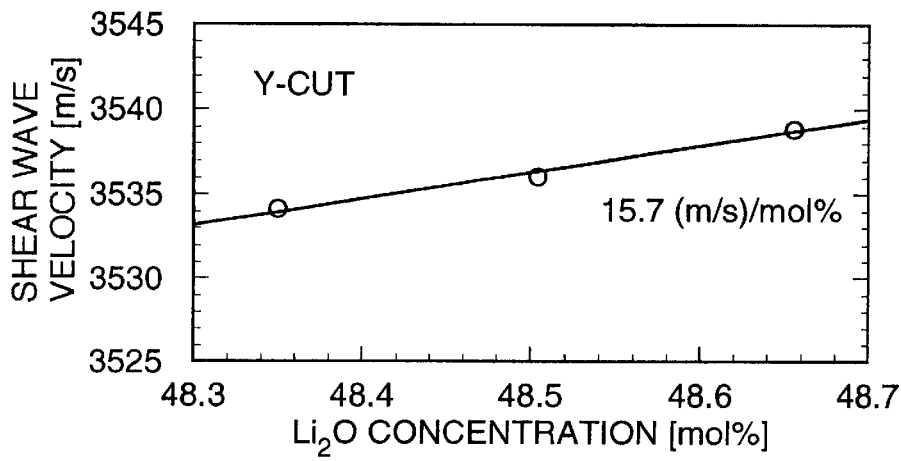
FIG. 5B is a graph showing measured values of the chemical composition dependence of shear wave velocities in the Y-cut LiTaO$_3$ specimens.
Figure 5C:
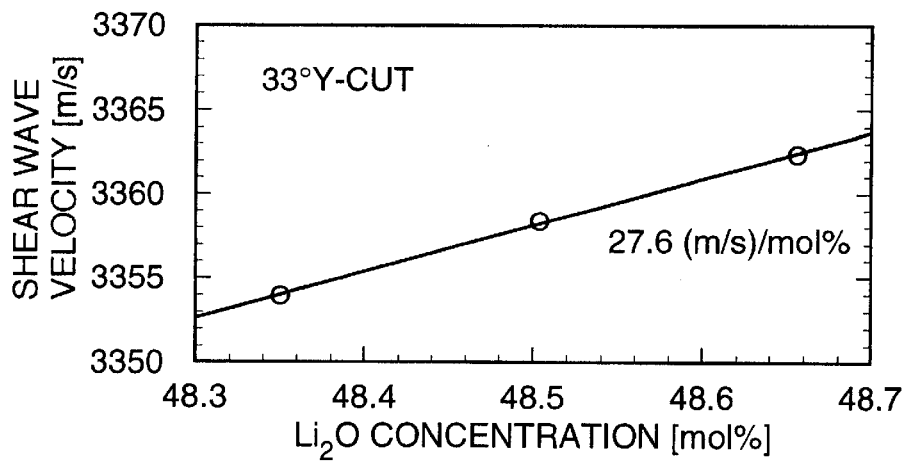
FIG. 5C is a graph showing measured values of the chemical composition dependence of shear wave velocities in the 33° Y-cut LiTaO$_3$ specimens.

To determine all independent components of the acoustical physical constants, it is necessary to measure acoustic velocities, dielectric constants and density (see [Literature 4], [Literature 5] and [Literature 6]). Now, a description for the LiTaO$_3$ single crystal will be given. The velocity measurements were conducted for plate specimens of X-, Y-, Z- and 33° Y-cut substrates centrally thereof at 23° C. For the LSAW, the velocity of a 90° rotated X-axis (simply described as 90° X-axis) propagating waves for the Y-, Z- and 33° Y-cut specimens was measured; for the longitudinal wave, the velocity of propagation in the substrate-thickness direction for the X-, Y-, Z- and 33° Y-cut specimens was measured; and for the shear wave, the velocity of propagation of an X-axis polarized wave in the substrate-thickness direction for the Y-, Z- and 33° Y-cut specimens was measured. The Li$_2$O concentration distribution is observed in the growth-axis direction of the crystal, and in this instance, since the velocity measurement positions on the respective specimens are in almost the same plane in the direction of the specimen diameter, the specimens can be regarded as having substantially the same chemical composition. The chemical composition dependences of the measured acoustic wave velocities are shown in FIGS. 3A, 3B and 3C (LSAW velocityies), FIGS. 4A, 4B and 4C (longitudinal wave velocities) and FIGS. 5A, 5B and 5C (shear wave velocities). As will be seen from these graphs, the velocity linearly increases with an increase in the Li$_2$O concentration, the lines being obtained by the least square method.

Figure 6:
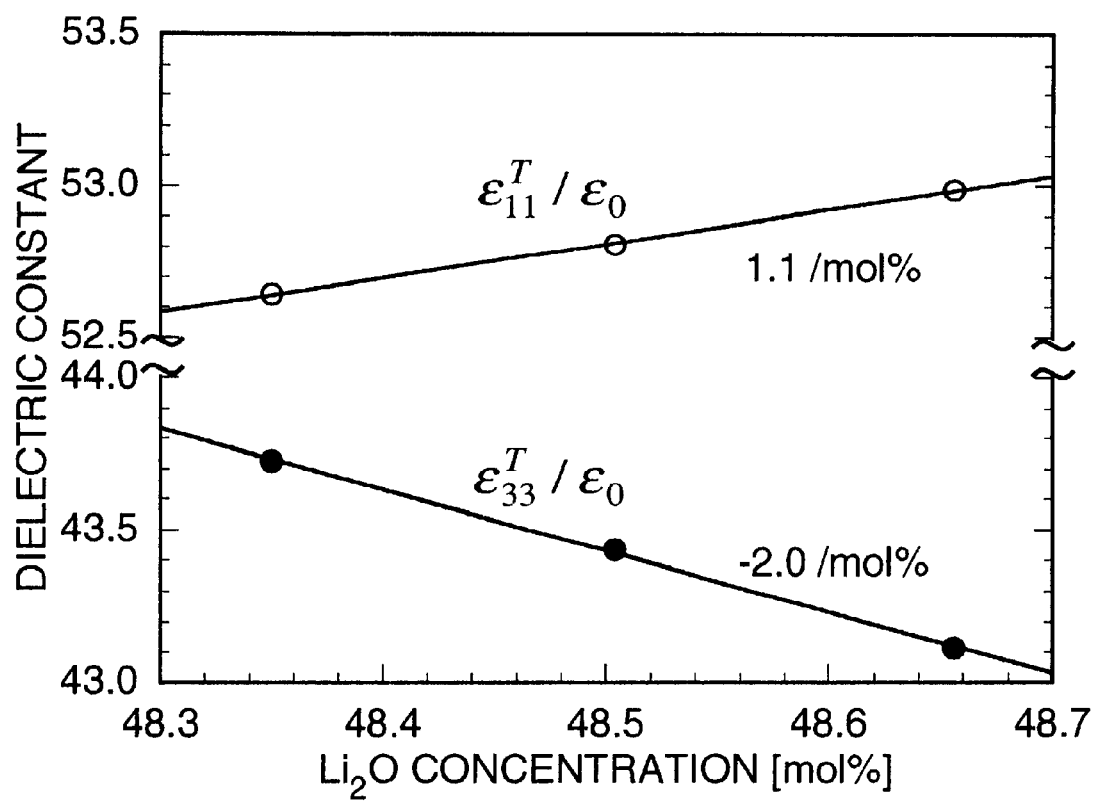
FIG. 6 is a graph showing measured values of the chemical composition dependence of the dielectric constants at constant stress of LiTaO$_3$ single crystals.

The dielectric constants ($\epsilon^T$) were measured under a constant stress. FIG. 6 shows the chemical composition dependences of the dielectric constants $\epsilon^T_{11}/\epsilon_0$ and $\epsilon^T_{33}/\epsilon_0$ measured for Y- and Z-cut substrate specimens, respectively.

It can be seen that the dielectric constants $\epsilon^T_{11}/\epsilon_0$ and $\epsilon^T_{33}/\epsilon_0$, though different in the direction of gradient, linearly change with the Li$_2$O concentration.

Figure 7:
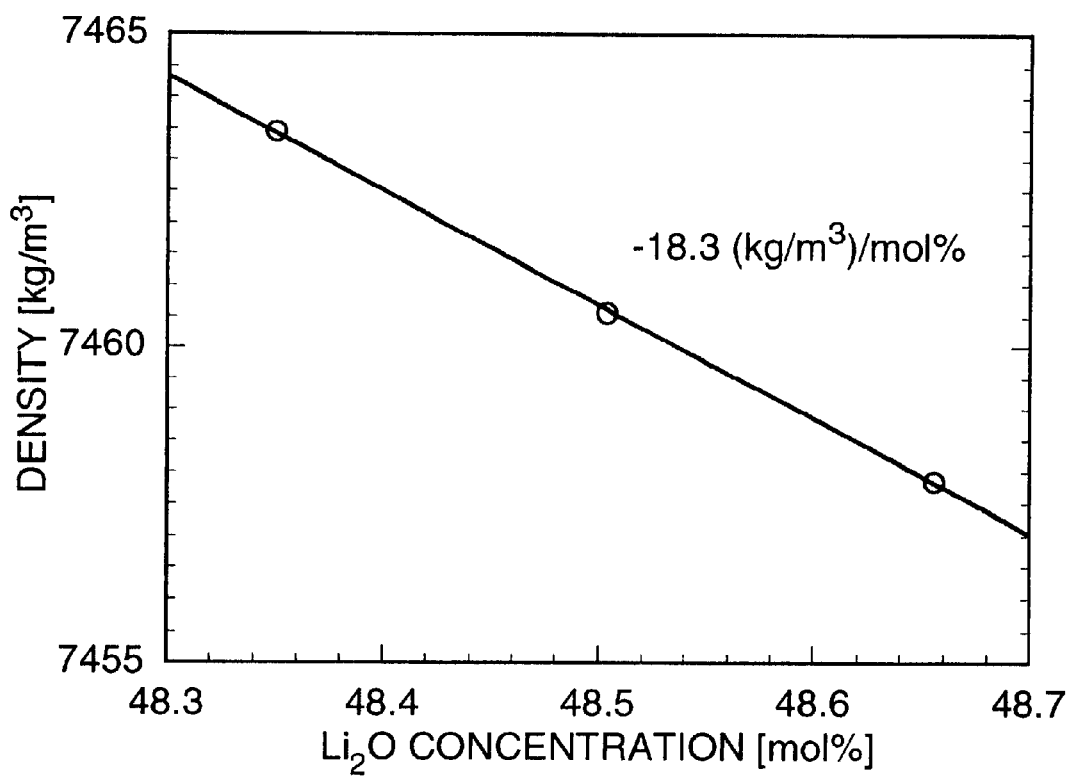
FIG. 7 is a graph showing measured values of the chemical composition dependence of the densities of a LiTaO$_3$ single crystal determined by the present invention.

The densities were measured for the Y-cut substrate specimens. FIG. 7 shows the chemical composition dependence of the density, which tends to linearly decrease with an increase in the Li$_2$O concentration.

Figure 8:
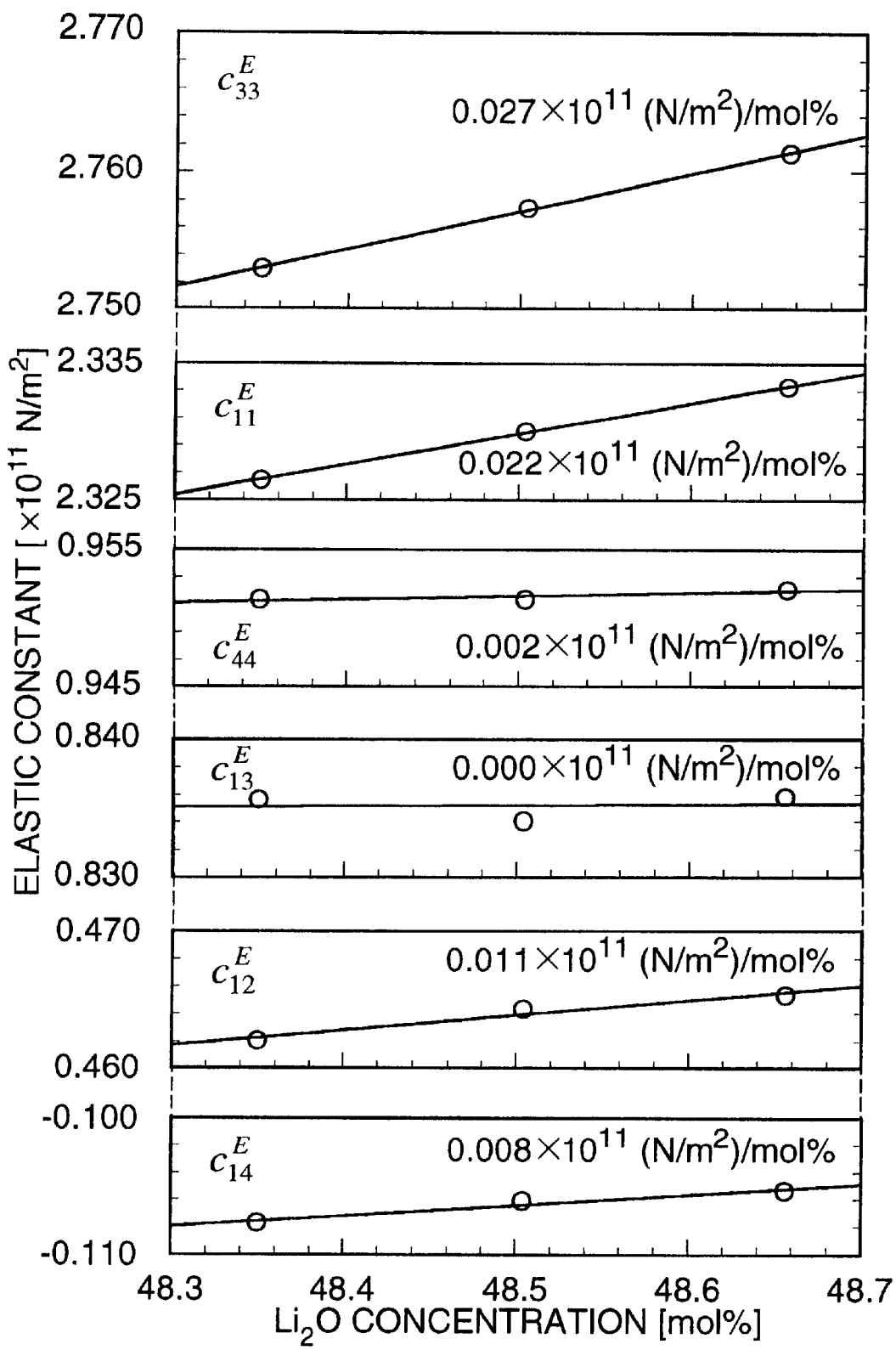
FIG. 8 is a graph showing measured values of the chemical composition dependences of the elastic stiffness constants at constant electric field of the LiTaO$_3$ single crystals determined by the present invention.
Figure 9:
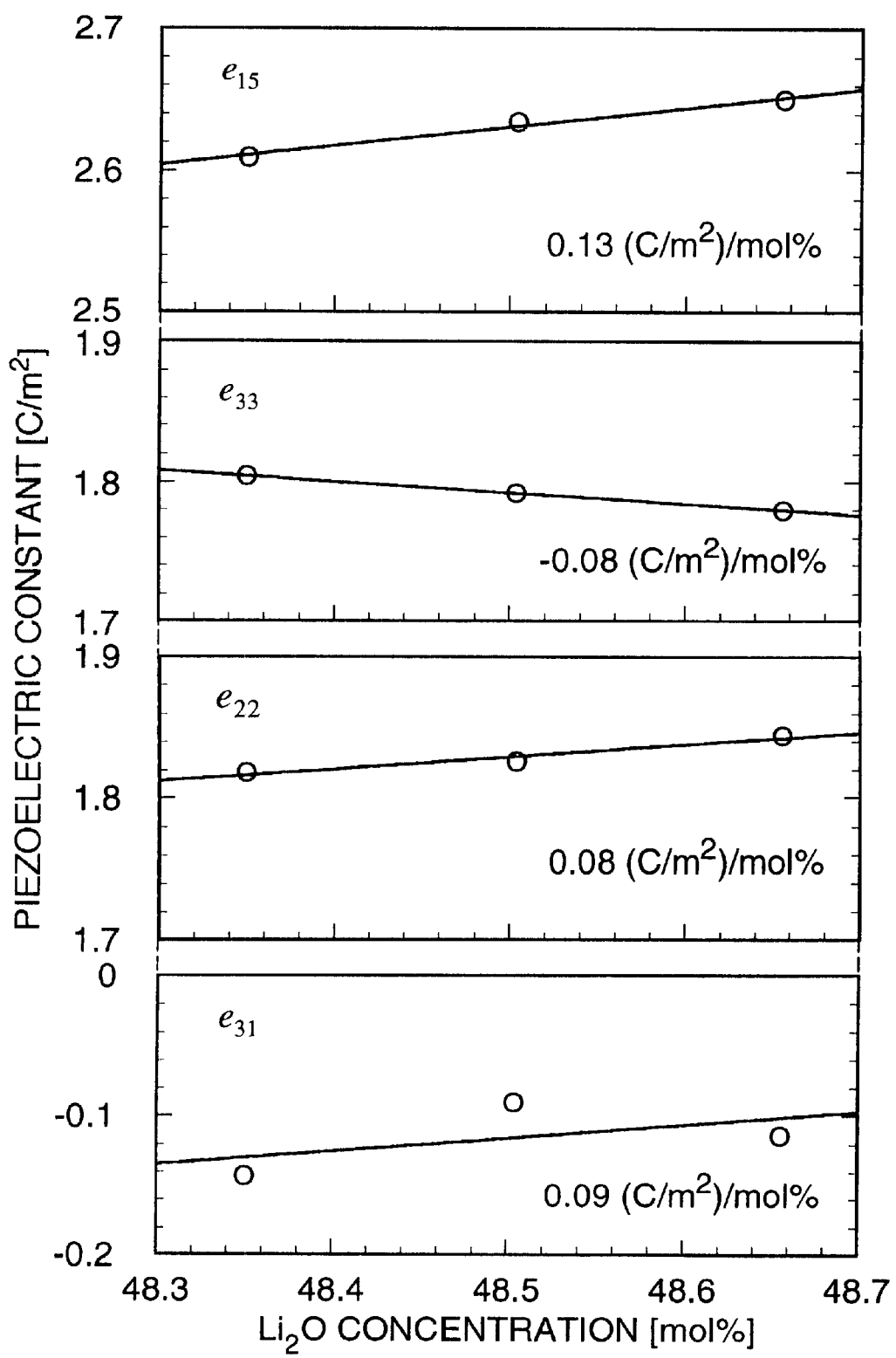
FIG. 9 is a graph showing measured values of the chemical composition dependences of the piezoelectric constants of the LiTaO$_3$ single crystals determined by the present invention.
Figure 10:
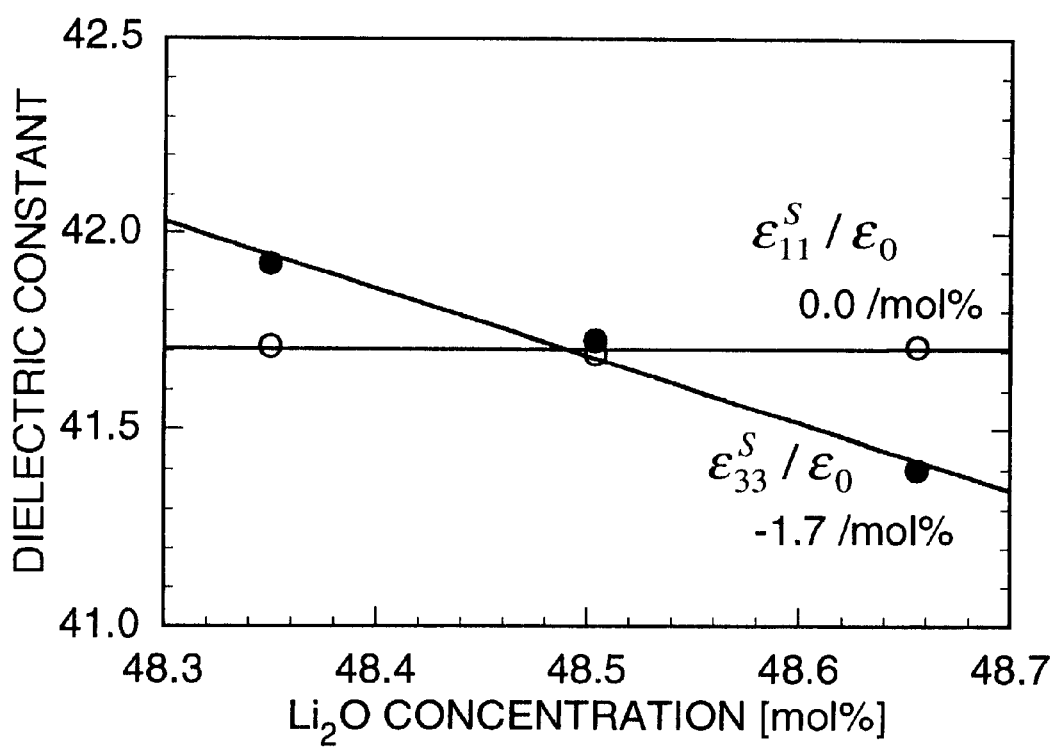
FIG. 10 is a graph showing measured values of the chemical composition dependences of the dielectric constants at constant strain of the LiTaO$_3$ single crystals determined by the present invention.

Based on such measured values as mentioned above, respective constants for three LiTaO$_3$ crystals with different chemical compositions were determined according to the acoustical physical constant determining methods set forth in [Literature 4], [Literature 5] and [Literature 6]. The thus determined values of the elastic stiffness constants at constant electric field, piezoelectric constants and dielectric constants at constant strain are shown in FIGS. 8, 9 and 10, respectively. Assuming that a measurement error for the Curie temperature is ±1° C., it is ±0.03 mol % in terms of a measurement error for the Li$_2$O concentration. Since the elastic constants, the piezoelectric constants, the dielectric constants and the densities all change linearly with the Li$_2$O concentration, it is possible to determine the constants for the LiTaO$_3$ with an arbitrary chemical composition around 48.5Li$_2$O-mol %. Table 2 of FIG. 11 shows the constants thus determined for the three single crystals and the gradients of the Li$_2$O concentration dependence of each constant.

Similarly, the acoustical physical constants for three LiNbO$_3$ single crystals with different chemical compositions were determined. Table 3 of FIG. 12 shows the determined constants and the gradient of the Li$_2$O concentration dependence of each constant. All the constants can be linearly approximated with the Li$_2$O concentration, and consequently, the constants of the LiNbO$_3$ of an arbitrary chemical composition around 48.4Li$_2$O-mol % can be determined.

With all of the acoustical physical constants determined by the procedure described above, the chemical composition dependences of the acoustic velocities (LSAW velocities, SAW velocities, longitudinal wave velocities and shear wave velocities) for an arbitrary substrate crystal plane and the direction and mode of propagation, and the interrelationships of velocities in various modes of propagation can be numerically calculated from the constants determined as described above.

EXAMPLES OF MEASUREMENTS

Three examples of the acoustic wave velocity measurements by the present invention will be described below.

Figure 13A:
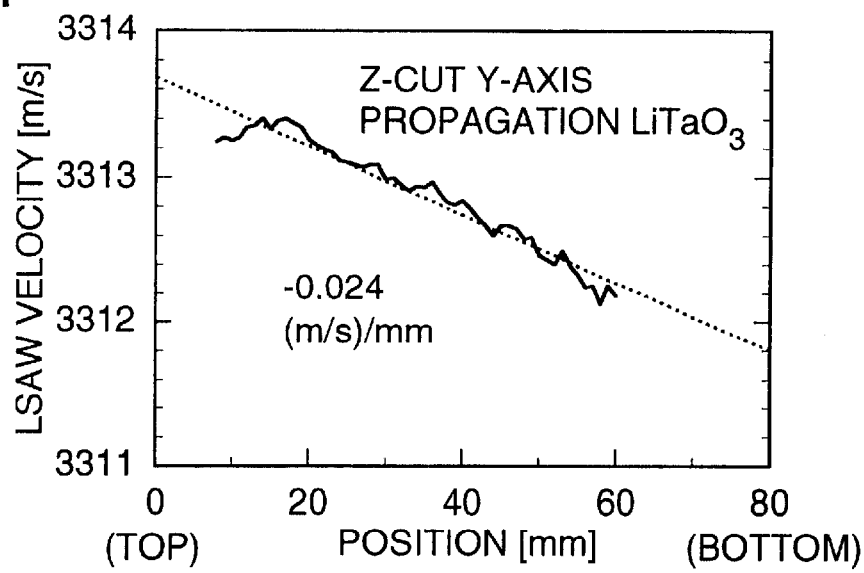
FIG. 13A is a graph showing the distribution of Y-propagating LSAW velocities on a Z-cut LiTaO$_3$ substrate prepared from the crystal ingot grown with a starting material composition of 48.0 Li$_2$O-mol % and the dotted approximated line for the measured results.
Figure 13B:
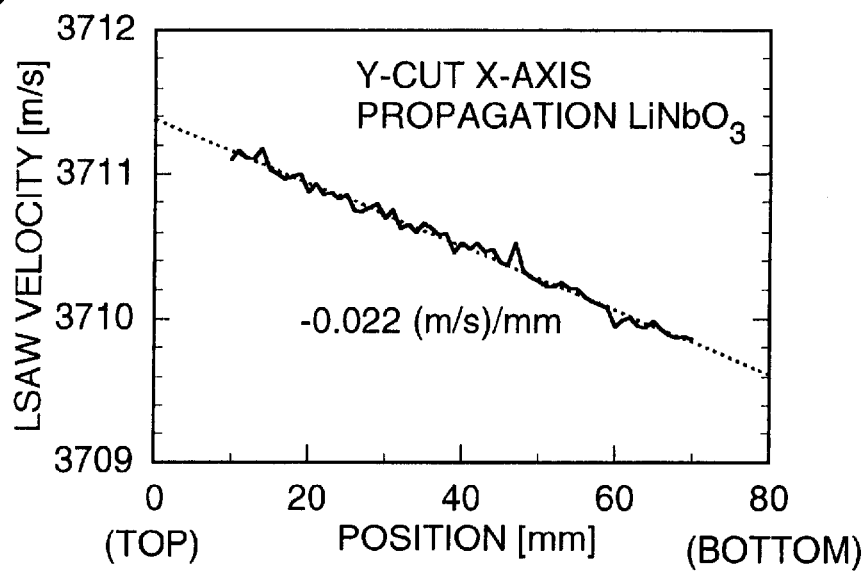
FIG. 13B is a graph showing the distribution of X-propagating LSAW velocities on a Y-cut LiTaO$_3$ substrate prepared from the crystal ingot grown with a starting material composition of 48.0 Li$_2$O-mol % and the dotted approximated line for the measured results.

A description will be given first of the case where the distribution of the chemical composition in a single crystal ingot is evaluated by the LSAW velocity measured in one substrate. Prepared as specimens in this example are a Z-cut LiTaO$_3$ single crystal substrate (the Z-cut plate in FIG. 2A) and a Y-cut LiNbO$_3$ single crystal substrate (the Y-cut plate in FIG. 2B) each grown from a starting material having a Li$_2$O concentration of 48.0 mol %. The LSAW velocity distribution is measured in the direction of the crystal growth axis. The LSAW propagation direction is the Y-axis direction for the Z-cut LiTaO$_3$ single crystal substrate and the X-axis direction for the Y-cut LiNbO$_3$ single crystal substrate. LSAW velocities were measured, at 1 mm intervals, on a straight line parallel to the crystal growth axis and passing through the center of the substrate. The measured values are shown as the solid lines in FIGS. 13A and 13B. The broken lines are approximated lines of the measured values. In either case, the LSAW velocities decrease almost linearly from the top of the crystal toward the bottom thereof, and the gradients of the LSAW velocities are −0.024 (m/s)/mm for the LiTaO$_3$ substrate and −0.022 (m/s)/mm for the LiNbO$_3$ substrate.

The gradients can be converted to those for the Li$_2$O concentration through utilization of the relationship between the LSAW velocity and the Li$_2$O concentration numerically calculated, as set forth in [Literature 8], from the constants in Table 2 determined according to the present invention, that is, by using the velocity of propagation in the Z-cut Y-axis direction for the LiTaO$_3$ single crystal, 28.0 (m/s)/Li$_2$O-mol %, and the velocity of propagation in the Y-cut X-axis direction for the LiNbO$_3$ single crystal, 26.6 (m/s)/Li$_2$O-mol %. In this case, the measured value of the chemical composition dependence of the LSAW velocity in the Z-cut Y-axis direction shown in FIG. 3A is available as the dependence of the LSAW velocity on the Li$_2$O concentration, and since the measured value matches the above-said numerically calculated value, either of them can be used as desired. The gradients of the LSAW velocities, −0.024 (m/s)/mm for the LiTaO$_3$ substrate and −0.022 (m/s)/mm for the LiNbO$_3$ substrate, are converted to −0.0008 Li$_2$O-mol %/mm and −0.0008 Li$_2$O-mol %/mm in terms of the gradients of the Li$_2$O concentration, respectively. From the converted gradients, it can be seen that the Li$_2$O concentration has reduced by 0.044 mol % and 0.048 mol % in the respective measuring ranges from the top of the crystal toward the bottom thereof.

Figure 14:
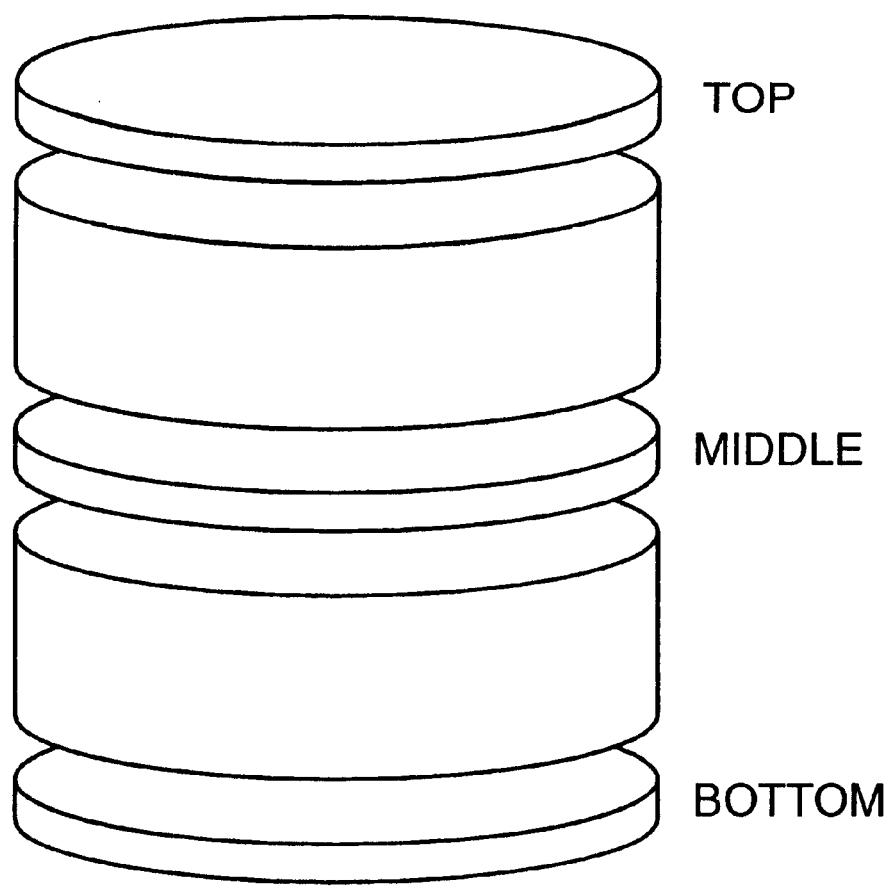
FIG. 14 is a diagram depicting an example of preparing substrate specimens having planes perpendicular to the axis of crystal growth.

Next, a description will be given of an example of estimating the chemical composition distribution in a crystal ingot from measured values of the longitudinal wave velocity. From top, middle and bottom sections of a SAW-grade LiTaO$_3$ single crystal ingot were cut, as specimens, three substrates (Y-cut plates) perpendicular to the direction of the crystal growth axis as depicted in FIG. 14. For each Y-cut substrate the velocity of propagation of the longitudinal wave in the direction of the substrate thickness was measured at the center of the substrate. The measured values are shown in Table 4 of FIG. 15, in which are also shown, for reference purposes, measured values of the LSAW velocity of X-axis propagation at the same point of measurement in the three Y-cut substrates. By converting the differences in the longitudinal wav velocity between the top substrate and the middle and bottom substrates to the differences in terms of the Li$_2$O concentration by use of the relationship, 44.7 (m/s)/Li$_2$O-mol %, between the velocity of propagation of the longitudinal wave in the Y-axis direction and the Li$_2$O concentration which was numerically calculated from the constants in Table 2 determined according to the present invention, it is estimated that the middle and bottom substrates are higher in the Li$_2$O concentration than the top substrate by 0.004 mol % and 0.020 mol %, respectively.

For verification purposes, by similarly converting the differences in the LSAW velocity between the top substrate and the middle and bottom substrates to the differences in terms of the Li$_2$O concentration by use of the value, 17.2 (m/s)/Li$_2$O-mol %, of the Li$_2$O concentration dependence of the LSAW velocity of propagation in the Z-axis of the Y-cut plate which was numerically calculated from the constants in Table 2 determined according to the present invention, it is estimated that the middle and bottom substrates are higher in the Li$_2$O concentration than the top substrate by 0.006 mol % and 0.023 mol %, respectively. These values are almost the same as those in the case of the longitudinal wave velocity. In this case, too, the experimentally measured values of the Li$_2$O concentration dependence of the velocity of the longitudinal wave in the Y-axis direction shown in FIG. 4C and the Li$_2$O concentration dependence of the LSAW velocity in the Y-cut X-axis direction shown in FIG. 3B are available; since these experimental results and the numerically calculated values match each other, they can be equally used.

Finally, a description will be given of an example for utilizing acoustic velocity measurements for the evaluation of a 42° rotated Y-cut (simply described as 42° Y-cut) LiTaO$_3$ single crystal used for SH-type SAW device substrates and the determination of the conditions for crystal growth.

Figure 16A:
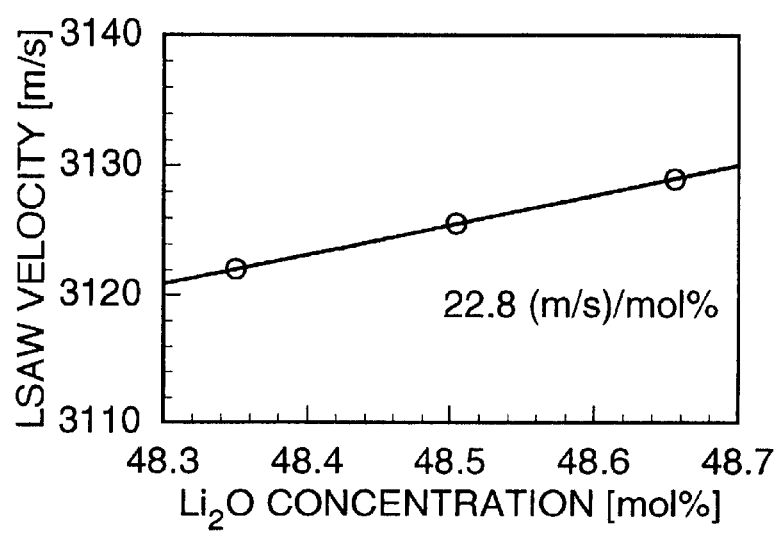
FIG. 16A is a graph showing the calculated relationship between the LSAW velocity and the Li$_2$O concentration for a 42° YX-LiTaO$_3$ single crystal.
Figure 16B:
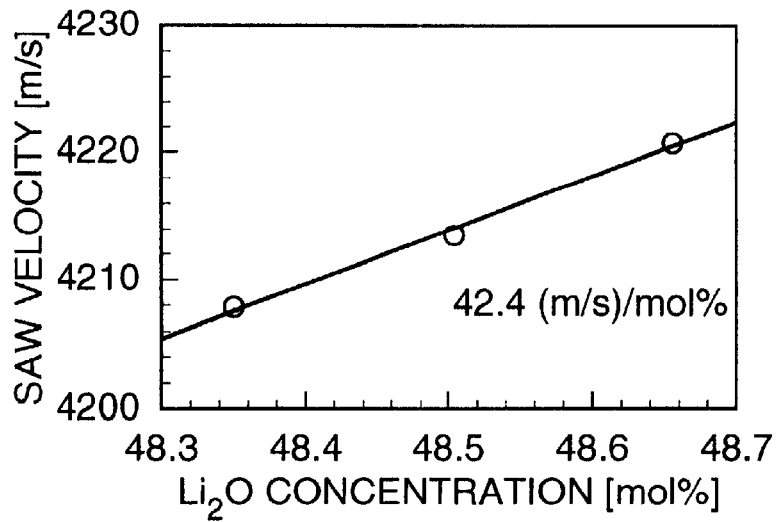
FIG. 16B is a graph showing the calculated relationship between the SH-type SAW velocity and the Li$_2$O concentration.
Figure 16C:
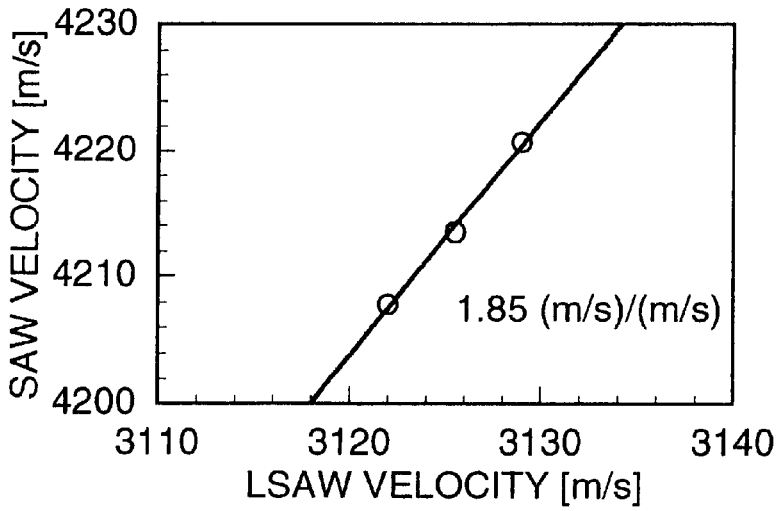
FIG. 16C is a graph showing the calculated relationship between the LSAW velocity and the SH-type SAW velocity.

The first step is to prepare a calibration line for detecting the chemical composition distribution in the crystal as the velocity distribution. FIGS. 16A, 16B and 16C show the chemical composition dependence of the LSAW velocity in the X-axis direction of a 42° Y-cut substrate (hereinafter referred to as a 42° YX-LiTaO$_3$ substrate) (FIG. 16A) and the chemical composition dependence of the SH-type SAW velocity (FIG. 16B) calculated from the constants in Table 2 according to [Literature 8] and [Literature 9], and the relationship between the LSAW velocity and the SH-type SAW velocity (FIG. 16C). The relationships between the LSAW velocity and the Li$_2$O concentration, between the SAW velocity and the Li$_2$O concentration, and between the LSAW velocity and the SH-type SAW velocity can be calculated to be 22.8 (m/s)/mol %, 42.4 (m/s)/mol % and 1.85 (SAW-m/s)/(LSAW-m/s) from the gradients of approximated lines, respectively.

Next, the LSAW velocity for 42° YX-LiTaO$_3$ single crystal specimens is measured using an LFB ultrasonic microscope. Used as the specimens are wafers cut from 42° Y-cut LiTaO$_3$ single crystal ingots of Manufacturers A and B. The Manufacturer-A specimens are a total of six wafers (about 75 mm in diameter and about 0.35 mm in thickness) cut from top and bottom sections of three crystal ingots with different lattice constants α. The Manufacturer-B specimens are a total of six wafers (about 75 mm in diameter and about 0.35 mm in thickness) cut from top and bottom sections of three crystal ingots with different Curie Temperatures. For all the specimens the LSAW velocities for the X-axis propagation were measured at five points spaced 10 mm apart in an area ±20 mm in the direction of the wafer diameter parallel to the X-axis. The measured values for the Manufacturer-A specimens are shown in FIG. 17, and the measured values for the Manufacturer-B specimens are shown in FIG. 18.

Figure 17:
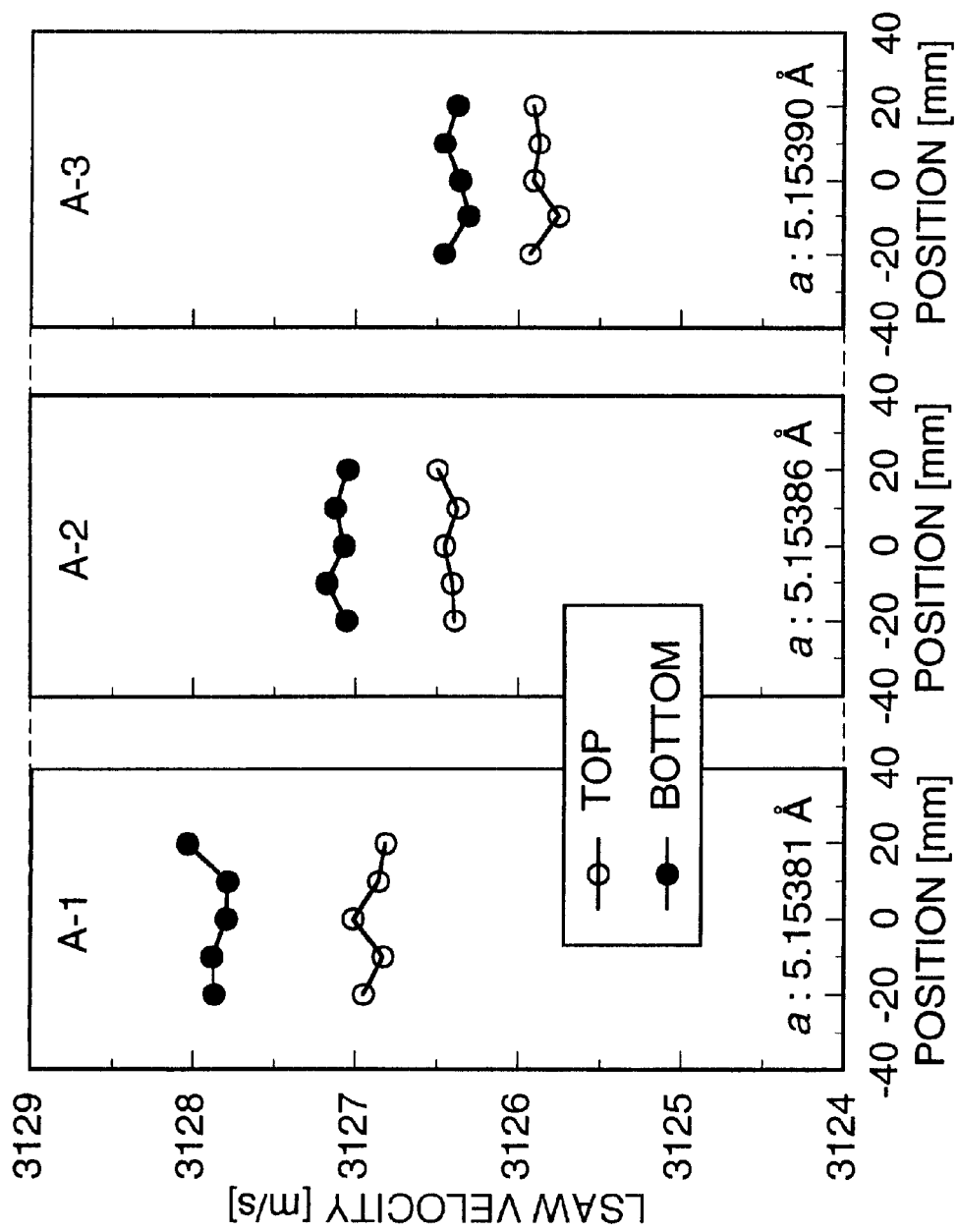
FIG. 17 shows measured values of the LSAW velocity distribution for two top and bottom wafers for each of three 42° YX-LiTaO$_3$ single crystal ingots of Manufacturer A.

In FIG. 17 the LSAW velocity distributions on the wafer surfaces are 0.13 to 0.25 m/s. In all the ingots the LSAW velocities for the substrates at the bottom section are higher than those for the substrates at the top section. As the lattice constant α increases, the LSAW velocity decreases, and the velocity difference between the substrates at the top and bottom sections decreases. In FIG. 18, the profiles on the wafer surfaces indicate that the LSAW velocities in the central portion of every specimen are higher than those in the peripheral portion thereof. The LSAW velocity distributions on the wafer surfaces are 0.13 to 0.18 m/s. It is common to all the crystal ingots that the substrates at the bottom section are higher in the LSAW velocity and the Curie temperature than the substrates at the top section. And there is a tendency that the LSAW velocity increases as the Curie temperature rises.

In Table 5 of FIG. 19 there are shown the interrelations between the LSAW velocity for the 42° YX-LiTaO$_3$ substrate and its other chemical and physical properties (lattice constant α, Curie temperature, Li$_2$O concentration and SAW velocity) that can be numerically calculated from the constants in Table 2 determined according to the present invention. As the lattice constant α in Table 5, a value of $-6.07\times10^{-5}$ Å/(m/s) is shown which was calculated from the gradient of the calibration line plotted as the relationship between average values of the LSAW velocities for the substrates at the bottom section and their lattice constants α since the lattice constant α in FIG. 17 was measured at a position relatively close to the bottom section substrate.

Figure 18:
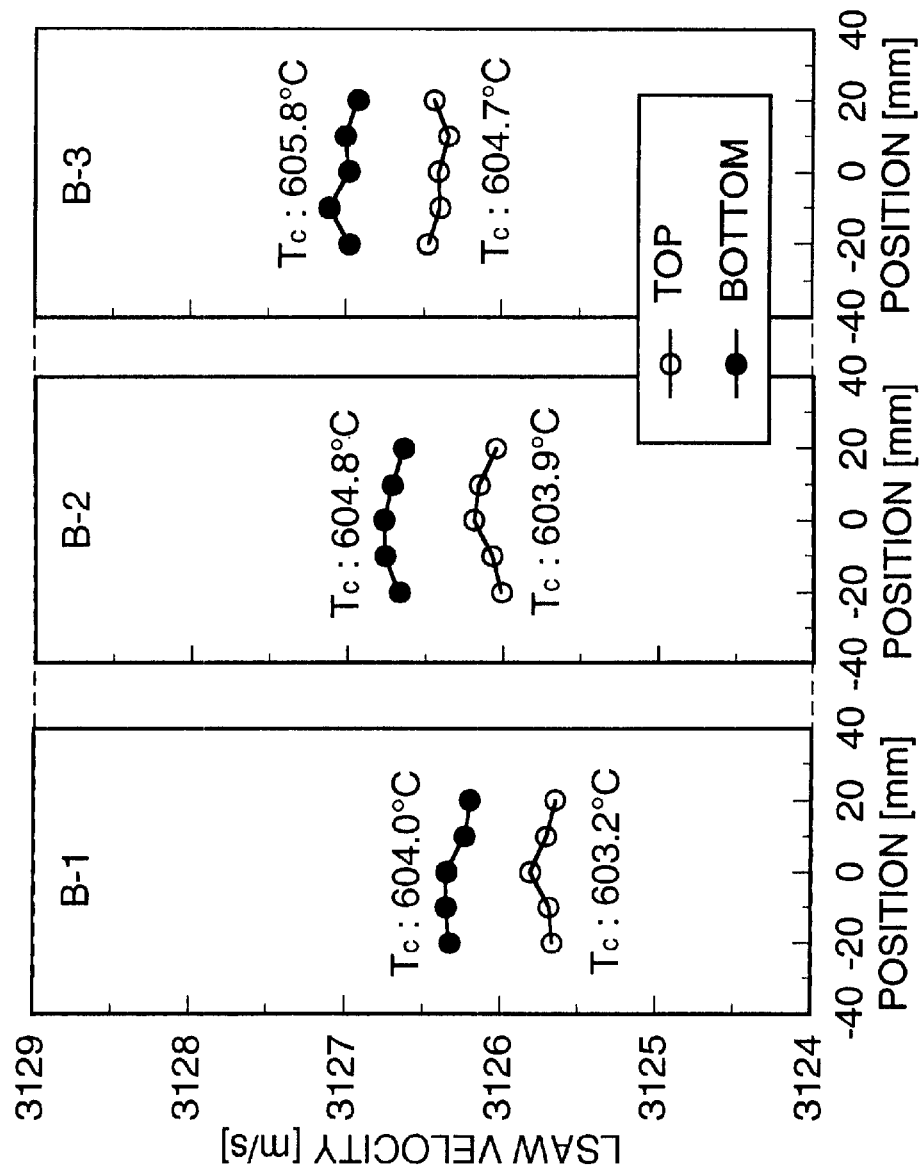
FIG. 18 shows measured values of the LSAW velocity distribution for two top and bottom wafers for each of three 42° YX-LiTaO$_3$ single crystal ingots of Manufacturer B.

By use of the relationships in Table 5, the LSAW velocity distributions shown in FIGS. 17 and 18 can be converted to the distributions of other chemical and physical properties. The distributions of the characteristic values classified in terms of "in wafer surface," "in ingot" and "among wafers" are shown in Table 6 of FIG. 20. With a permissible SAW velocity distribution of ±0.04% [Literature 10] defined as a reference, the SAW velocity distribution of ±0.04% corresponds to ±1.69 m/s. It can be seen that the "in wafer surface" distributions and the "in ingot" distributions of the both manufacturers and the "among wafers" distribution of Manufacturer B are all inside the acceptable limits but that "among wafers" distributions of Manufacturer A are outside the acceptable limits.

Next, the amount of change in the LSAW velocity in the growth-axis direction of the crystal B-1 in FIG. 18 (a crystal grown from a starting material having a $Li_2O$ concentration of 48.52 mol %) is used to determine the conditions (in particular, the chemical composition of the starting material) for the growth of a more homogeneous crystal. By using a difference 0.59 m/s between average values of the LSAW velocities for the top and bottom section wafers cut from the crystal B-1 in FIG. 18 and the distance 120 mm between the both wafer cutting sections, the gradient of the LSAW velocity in the growth-axis direction (from the top of the crystal toward the bottom thereof) can be estimated to be 0.0049 (m/s)/mm. Converted to the gradient of the $Li_2O$ concentration by use of the relationship, 22.8 (m/s)/$Li_2O$-mol %, between the $Li_2O$ concentration and the LSAW velocity in FIG. 16A determined by numerical calculation, the LSAW velocity gradient is +0.0002 $Li_2O$-mol %/mm.

Figure 21A:
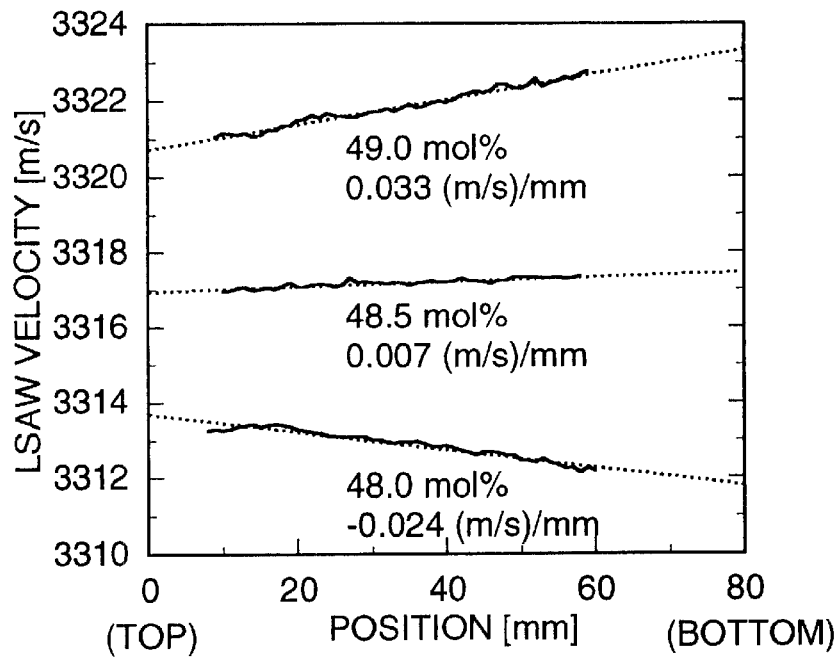
FIG. 21A is a graph showing measured values of Y-propagating LSAW velocity distributions in the growth-axis direction of Z-cut substrates of LiTaO$_3$ crystals grown from starting materials having Li$_2$O concentrations of 48.0, 48.5 and 49.0 mol % and the dotted approximated lines for the measured results.
Figure 21B:
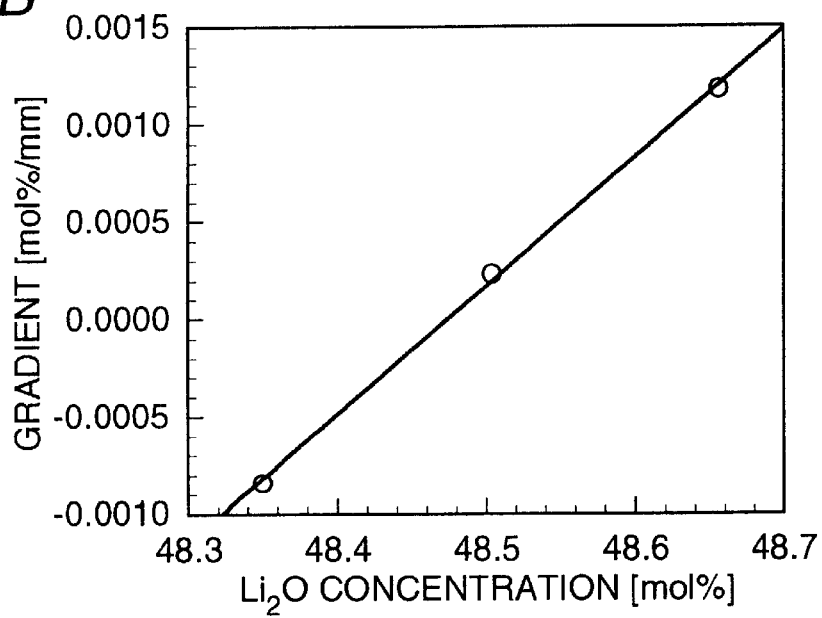
FIG. 21B is a graph showing the relationship between the Li$_2$O concentration gradient in the growth-axis direction of each crystal obtained in FIG. 21A and the Li$_2$O concentration calculated from the Curie temperature.

On the other hand, the gradients of the $Li_2O$ concentration in the growth-axis direction for the three single crystal ingots used to determine the constants according to the present invention are estimated to be −0.0008, +0.0002 and +0.0012 $Li_2O$-mol %/mm, respectively, from the measured values of the LSAW velocity in the Y-axis direction on the Z-cut substrates of the respective ingots (see FIG. 21A [Literature 7]). The relationship (FIG. 21B) between these gradients and the $Li_2O$ concentrations in Table 1 is used to calculate the $Li_2O$ concentration that reduces the gradient in the growth-axis direction to zero. From the approximated line in FIG. 21B can be calculated a $Li_2O$ concentration of 48.47 mol % at which the gradient in the growth-axis direction becomes zero.

Figure 22:
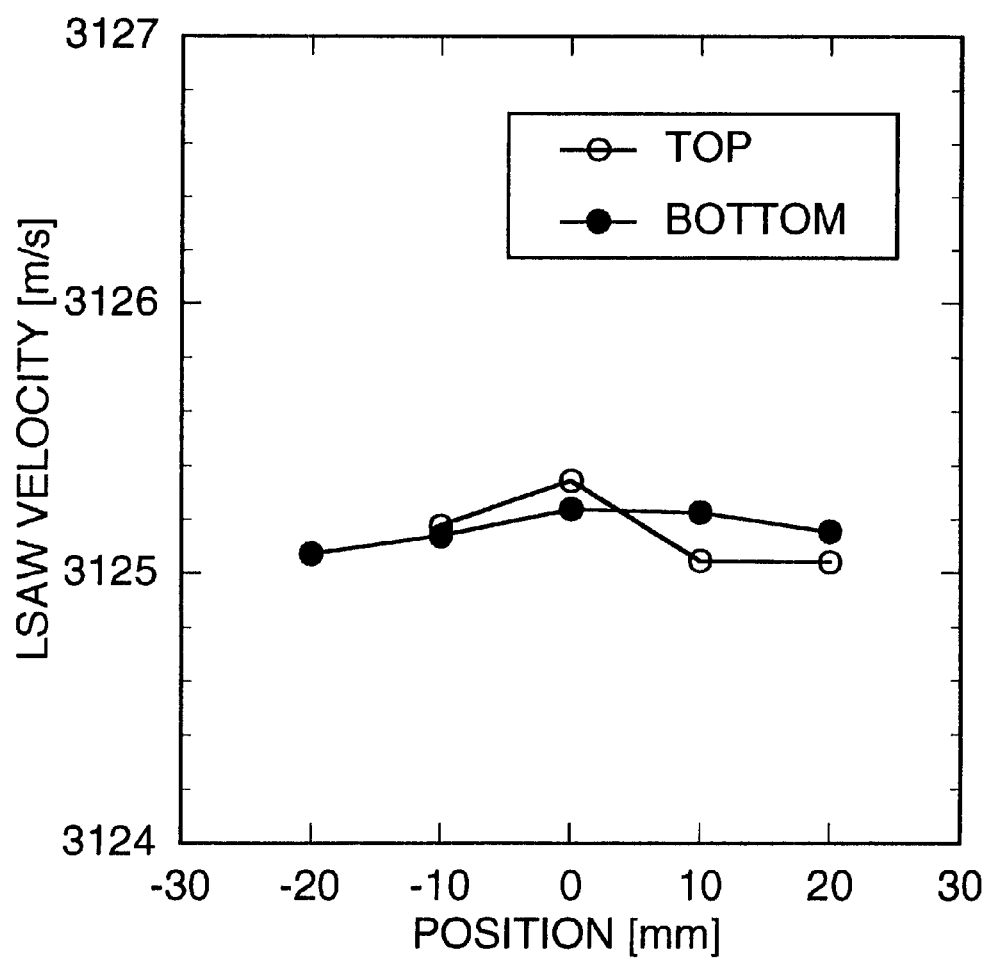
FIG. 22 is a graph showing the LSAW distributions in wafer specimens cut from top and bottom sections of a 42° YX-LiTaO$_3$ single crystal grown from a starting material with a reduced Li$_2$O concentration.

Then, a conversion coefficient α is experimentally determined which is used to calculate an increase or decrease in the $Li_2O$ concentration of the starting material to grow crystals with increased homogeneity under any growth conditions close to a congruent composition. In this example, α=209. Since the coefficient α somewhat varies according to crystal growth conditions (crystal-growing furnace, number of rotations of a seed crystal, crystal pulling speed, in-furnace temperature distribution, and so forth), it is considered necessary to experimentally determine the coefficient α for each growth condition. It is estimated that 0.05 $Li_2O$-mol %, obtainable by multiplying the $Li_2O$ concentration gradient of +0.0002 $Li_2O$-mol %/mm for the crystal B-1 in FIG. 18 by the coefficient α, needs only to be subtracted from the $Li_2O$ concentration of the starting material. Accordingly, it is recommended to grow the crystal from a starting material with a $Li_2O$ concentration of 48.47 mol %. FIG. 22 shows the measured results of the LSAW velocity distribution in a crystal grown under the improved growth conditions. As will be seen from FIG. 22, the LSAW velocity difference between the to—and bottom section substrates is reduced—this indicates that a suitable selection of the $Li_2O$ concentration provides increased homogeneity in the crystal growth.

Figure 23B:
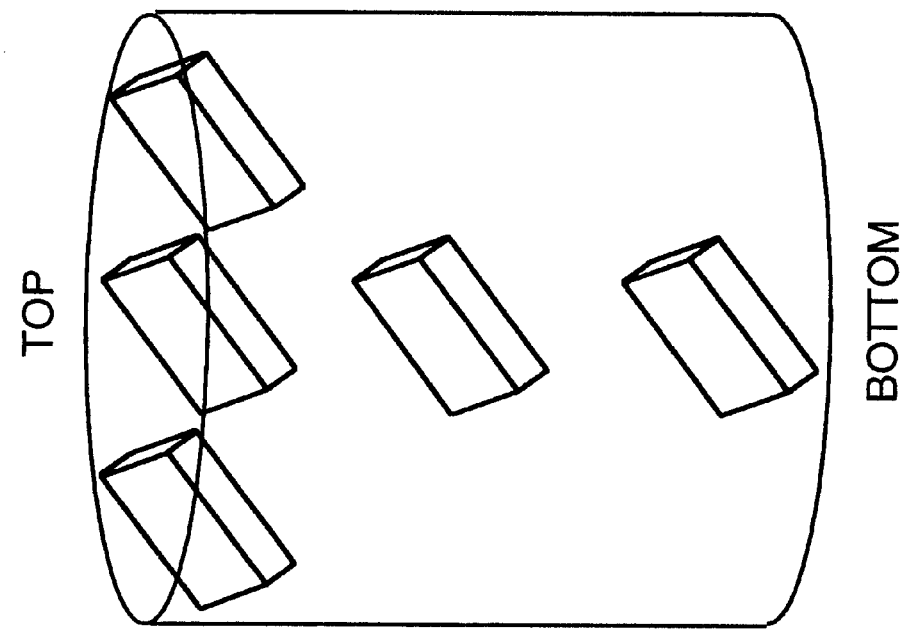
FIG. 23B is a diagram showing another example of substrate specimens prepared for evaluating the chemical composition distributions in the directions of growth axis and diameter of a single crystal ingot.
Figure 23A:
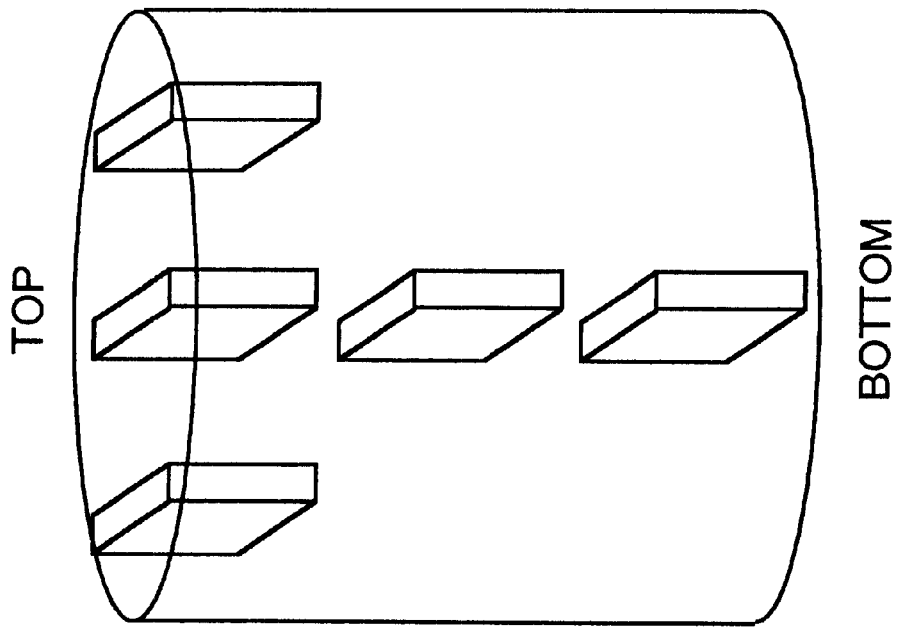
FIG. 23A is a diagram showing an example of substrate specimens prepared for evaluating the chemical composition distributions in the directions of growth axis and diameter of a single crystal ingot.

The specimens for evaluating the chemical composition distributions in crystal ingots can be cut therefrom along the vertical axis as shown in FIG. 2 or into round slices as shown in FIG. 14; further, specimens can be cut from crystal ingots as shown in FIG. 23A or 23B so as to examine the chemical composition in the direction of the specimen diameter and in the growth-axis direction in various crystal planes. In some cases, the substrate material is evaluated by use of the acoustic velocity of propagation for the substrate having the same crystal plane as that actually used for SAW devices as described above; crystal planes for which the amount of change in the acoustic velocity with the chemical composition is larger, that is, crystal planes for which the directions and modes of propagation of acoustic waves are sensitive to a change in the chemical composition, can be numerically calculated from the constants determined according to the present invention.

The measurement of the Curie temperature encounters such a problem as mentioned below.

Figure 24:
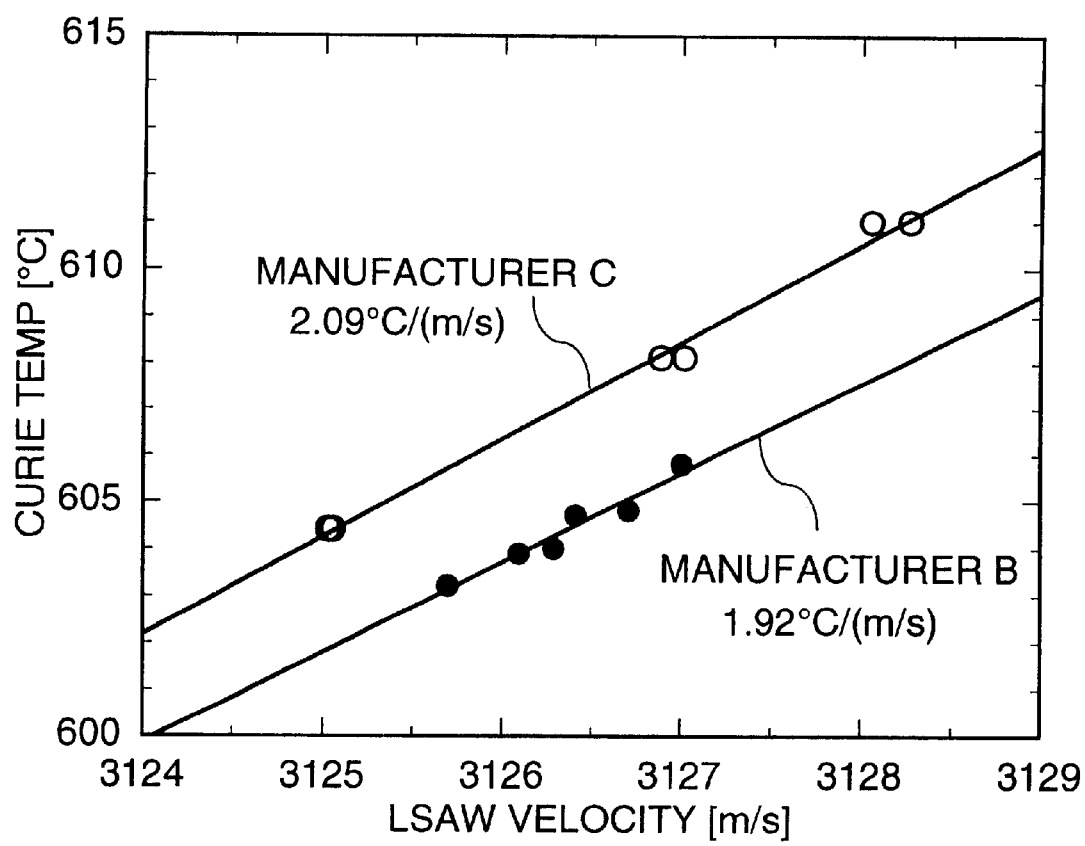
FIG. 24 is a graph showing the relationship between measured values of the LSAW velocity in 42° YX-LiTaO$_3$ single crystal wafers by Manufacturers B and C and their measured values of the Curie temperature, the solid lines being approximated lines.

FIG. 24 shows plots of the LSAW velocity for 42° YX-$LiTaO_3$ substrates of Manufacturers B and C measured by use of an LFB ultrasonic microscopy and their Curie temperatures measured by the both manufacturers, together with approximated lines of the plots. The gradients of the both approximated lines are 1.92° C./(m/s) and 2.09° C./(m/s), respectively. The gradients are very close in value to each other, but it can be seen that they differ about 2° C.(0.33%) in terms of the Curie temperature. This is considered to be caused by different conditions for the measurement of the Curie temperature by the different manufacturers and measurement errors between their measuring instruments. According to the present invention, the absolute accuracy of measurement of the LSAW velocity and the measurement repeatability are as high as ±0.01% and ±0.002%, respectively. Hence, the absolute accuracy of the Curie temperature measuring instrument can be increased by calibrating the absolute value of the Curie temperature based on the LSAW velocity. In this instance, the longitudinal wave, shear wave, or SAW velocity can also be measured for the calibration of the Curie temperature.

Based on the embodiments described above, a basic procedure of the single crystal evaluation according to the present invention will be described below with reference to FIG. 25.

In the following description, reference character "v" indicates the acoustic velocity in an arbitrary mode of propagation and "$v_i$" indicates the acoustic velocity in any one of the following propagation modes.

$v_{LSAW}$: LSAW velocity, $v_{SAW}$: SAW velocity, $v_L$: longitudinal wave velocity, $v_S$: shear wave velocity Step S1:

Prepare a plurality of single crystals with different nominal chemical compositions.

Step S2:

Measure a physical property (Curie temperature or lattice constant) of each single crystal, and calculate a true chemical composition D of said each single crystal by use of a known relationship between the measured physical property and the chemical composition.

Step S3:

Prepare, from the single crystals, substrates each having a desired crystal plane for the determination of acoustical physical constants.

Step S4:

Measure the acoustic velocity v ($v_{LSAW}$, $v_L$, $v_S$) in a desired propagation mode for each of the substrates of different chemical compositions and some acoustical physical constants c (dielectric constants, density) of said each substrate, and determine acoustical physical constants c (elastic constants, piezoelectric constants, dielectric constants, density) for the respective single crystals by known calculation methods.

Evaluation 1

Step S5-1:

Calculate acoustic velocity v' for a desired crystal plane of each substrate and in a desired propagation direction with respect to the true chemical composition D by a known method through use of the acoustical physical constants c determined as mentioned above.

Step S6-1:

Calculate a gradient $g=\Delta v'/\Delta D$ of the acoustic velocity v' calculated in step S5-1 with respect to the true chemical composition D.

Step S7-1:

Measure the distribution of acoustic velocity v" for the specimen to be evaluated, and calculate the amount of change in the chemical composition, $\Delta D''=\Delta v''/g$, of the chemical composition by use of the gradient g calculated in step S6-1.

Step S8-1:

Calculate, for example, the gradient, $\Delta D''/\Delta L$, of the chemical composition in the direction of the crystal growth axis, and feed it back to the conditions for crystal growth as required.

Evaluation 2

Step S5-1:

Calculate acoustic velocity v' for a desired crystal plane of each substrate and in a desired propagation direction with respect to the true chemical composition D by a known method through use of the acoustical physical constants c determined as mentioned above.

Step S6-2:

Calculate the gradient, $g_{kj}=\Delta v'_k/\Delta v'_j$, of $v'_k$ against $v'_j$ from the calculated result in step S5-1.

Step S7-2:

Measure the distribution of acoustic velocity $v''_j$ for the specimen to be evaluated, and calculate the amount of change, $\Delta v''_k=g_{kj}\Delta v''_j$, of the acoustic velocity in a different mode and direction of propagation by use of the gradient $g_{kj}$ calculated in sep S6-2.

Evaluation 3

Step S5-3:

Calculate acoustical physical constants c' with respect to a desired chemical composition D' from an approximated line of plotted values of the acoustical physical constants c determined with respect to the true chemical composition D.

Step S6-3:

Calculate the acoustic velocity v in an arbitrary propagation mode for the substrate from measured value of its Curie temperature $T_C$ or lattice constant $\alpha$.

EFFECT OF THE INVENTION

As described above, the present invention enables the calibration line of acoustic velocity against the chemical composition to be directly obtained by numerical calculation for each of the substrate crystal plane, and the direction and mode of propagation, permitting efficient evaluation of materials. Further, the relationships between acoustic velocities (between longitudinal and shear waves, and between SAW and LSAW) in respective propagation modes for an arbitrary chemical composition can also be obtained by numerical calculation. Since the present invention permits efficient evaluation of material properties by acoustic velocity measurements, the evaluation made so far by the lattice constant or Curie temperature can be conducted directly by use of acoustic velocity. By using a calibrated Curie temperature, lattice constant or chemical composition, it is possible to obtain the SAW velocity related directly to the evaluation of SAW device materials. Furthermore, the gradient of the chemical composition in a single crystal ingot can easily be obtained, and by utilizing the gradient for improving the chemical composition of the starting material that is one of the conditions for crystal growth, it is possible to grow a crystal with uniform chemical composition (or elastic properties or similar physical properties) throughout the crystal ingot.

REFERENCE LITERATURE

[Literature 1] J. Kushibiki and N. Chubachi, "Material characterization by line-focus-beam acoustic microscope," IEEE Trans. Sonics and Ultrason., vol. SU-32, pp. 189–212 (1985).

[Literature 2] M. Sato, A Iwama, J. Yamada, M. Hikita, and Y. Furukawa, "SAW velocity variation of $LiTaO_3$ substrates," Jpn. J. Appl. Phys., vol. 28, Suppl. 28-1, pp. 111–113 (1989).

[Literature 3] K. Yamada, H. Takemura, Y. Inoue, T. Omi, and S. Matsumura, "Effect of Li/Nb ratio on the SAW velocity of 128° Y-X $LiNbO_3$ wafers," Jpn. Appl. Phys., vol. 26, Suppl. 26-2, pp. 219–222 (1987).

[Literature 4] J. Kushibiki, I. Takanaga, M. Arakawa, and T. Sannomiya, "Accurate measurements of the acoustical physical constants of $LiNbO_3$ and $LiTaO_3$ single crystals," IEEE Trans. Ultrson., Ferroelect., Freq. Contr., Vol. 46, pp. 1315–1323 (1999).

[Literature 5] I. Takanaga and J. Kusibiki, "A method of determining acoustical physical constants for piezoelectric materials by line-focus-beam acoustic microscopy," 20th Ultrason. Symp. Proc., pp. 125–126 (1999).

[Literature 6] I. Takanaga and J. Kusibiki, "A method of determining acoustical physical constants for piezoelectric materials by line-focus-beam acoustic microscopy," Technical Report of IEICE, US99-38, pp. 9–16 (1999).

[Literature 7] J. Kushibiki, T. Okuzawa, J. Hirohashi, and Y. Ohashi, "Line-focus-beam acoustic microscopy characterization of optical-grade $LiTaO_3$ single crystals," J. Appl. Phys., Vol. 87, pp. 4395–4403 (2000).

[Literature 8] J. J. Campbell and W. R. Jones, "Propagation of surface waves at the boundary between a piezoelectric crystal and a fluid medium," IEEE Trans. Sonics and Ultrason., Vol. SU-17, pp. 71–76 (1970).

[Literature 9] J. J. Campbell and W. R. Jones, "A method for estimating optimal crystal cuts and propagation directions for excitation of piezoelectric surface waves," IEEE Trans. Sonics and Ultrason., Vol. SU-15, pp. 209–217 (1968)

[Literature 10] K. Yamada, T. Omi, S. Matsumura, and T. Nishimura, "Characterization of 4-inch $LiTaO_3$ single crystals for SAW device application," IEEE Ultrason. Symp. Proc., pp. 243–248 (1984).

What is claimed is:

1. A method for material evaluation by acoustic velocity measurements, comprising the steps of:
   (a) preparing a plurality of acoustical physical constants determining materials with different nominal chemical compositions;
   (b) measuring one of the Curie temperature and lattice constant of each of said acoustical physical constant determining materials as a physical property, and calculating a true chemical composition D of said each acoustical physical constant determining material by use of a known relationship between said physical property and said chemical composition;
   (c) preparing, from said each acoustical physical constant determining material, substrates for determining desired acoustical physical constants;
   (d) measuring the acoustic velocities v ($v_{LSAW}$, $v_L$, $v_S$), dielectric constants and density for said acoustical physical constant determining substrates of different chemical compositions, and determining elastic and piezoelectric constants as acoustical physical constants of said each acoustical physical constant determining material based on measured values of said acoustic velocities, dielectric constants and density; and
   (e) measuring the acoustic velocities of a material to be evaluated, converting the measured values to desired parameters based on said acoustical physical constants, and evaluating said material based on said parameters, wherein step (e) comprises:
      (e-1) calculating acoustic velocity v' for a desired cut specimen plane of said material, for a desired propagation mode and for a desired propagation direction with respect to said true chemical composition D by a known method through use of said determined acoustical physical constants;
      (e-2) calculating a gradient $g=\Delta v'/\Delta D$ of the acoustic velocity v' calculated in said step (e-1) with respect to said true chemical composition D; and
      (e-3) measuring the distribution of acoustic velocity v" for the specimen to be evaluated, and calculating the amount of change, $\Delta D''=\Delta v''/g$, of the chemical composition by use of said gradient g calculated in said step (e-2).

2. The method of claim 1, wherein said material is a single crystal material, and said step (e) further comprises a step of calculating, for example, a gradient $\Delta D''/\Delta L$ of the chemical composition with respect to distance L in the direction of the crystal growth axis, and feeding back said gradient $\Delta D''/\Delta L$ to the conditions for crystal growth as required.

3. A method for material evaluation by acoustic velocity measurements, comprising the steps of:
   (a) preparing a plurality of acoustical physical constants determining materials with different nominal chemical compositions;
   (b) measuring one of the Curie temperature and lattice constant of each of said acoustical physical constant determining materials as a physical property, and calculating a true chemical composition D of said each acoustical physical constant determining material by use of a known relationship between said physical property and said chemical composition;
   (c) preparing, from said each acoustical physical constant determining material, substrates for determining desired acoustical physical constants;
   (d) measuring the acoustic velocities v ($v_{LSAW}$, $v_L$, $v_S$), dielectric constants and density for said acoustical physical constant determining substrates of different chemical compositions, and determining elastic and piezoelectric constants as acoustical physical constants of said each acoustical physical constant determining material based on measured values of said acoustic velocities, dielectric constants and density; and
   (e) measuring the acoustic velocities of a material to be evaluated, converting the measured values to desired parameters based on said acoustical physical constants, and evaluating said material based on said parameters, wherein step (e) comprises:
      (e-1) calculating acoustic velocity v' for a desired cut specimen plane of said material, for a desired propagation mode and for a desired propagation direction with respect to said true chemical composition D by a known method through use of said determined acoustical physical constants;
      (e-2) calculating a gradient, $g_{kj}=\Delta v'_k/\Delta v'_j$, of $v'_k$ with respect to $v'_j$ from the calculated result in step (e-1); and
      (e-3) measuring the distribution of acoustic velocity $v''_j$ for the specimen to be evaluated, and calculating the amount of change, $\Delta v''_k = g_{kj}\Delta v''_j$, of the acoustic velocity in a different mode and direction of propagation by use of said gradient $g_{kj}$ calculated in sep (e-2).

4. A method for material evaluation by acoustic velocity measurements, comprising the steps of:
   (a) preparing a plurality of acoustical physical constants determining materials with different nominal chemical compositions;
   (b) measuring one of the Curie temperature and lattice constant of each of said acoustical physical constant determining materials as a physical property, and calculating a true chemical composition D of said each acoustical physical constant determining material by use of a known relationship between said physical property and said chemical composition;
   (c) preparing, from said each acoustical physical constant determining material, substrates for determining desired acoustical physical constants;
   (d) measuring the acoustic velocities v ($v_{LSAW}$, $v_L$, $v_S$), dielectric constants and density for said acoustical physical constant determining substrates of different chemical compositions, and determining elastic and piezoelectric constants as acoustical physical constants of said each acoustical physical constant determining material based on measured values of said acoustic velocities, dielectric constants and density; and
   (e) measuring the acoustic velocities of a material to be evaluated, converting the measured values to desired parameters based on said acoustical physical constants, and evaluating said material based on said parameters, wherein step (e) comprises:
      (e-1) calculating acoustical physical constants c' with respect to a desired chemical composition D' from an approximated line of plotted values of said acoustical physical constants c determined with respect to said true chemical composition D; and
      (e-2) calculating the acoustic velocity v in an arbitrary propagation mode for said each specimen from measured value of said physical property.

5. The method of any one of claims 1, 2, 3 or 4, wherein said desired physical property is Curie temperature.

6. The method of claim 5, wherein said material is a $LiTaO_3$ single crystal.

7. The method of claim 5, wherein said material is a LiNbO$_3$ single crystal.

8. The method of any one of claims 1, 2, 3 or 4, wherein said physical property is lattice constant.

9. The method of claim 8, wherein said material is a LiTaO$_3$ single crystal.

10. The method of claim 8, wherein said material is a LiNbO$_3$ single crystal.

11. The method of any one of claims 1, 2, 3 or 4, wherein said physical property is chemical composition.

12. The method of claim 11, wherein said material is a LiTaO$_3$ single crystal.

13. The method of claim 11, wherein said material is a LiNbO$_3$ single crystal.

14. A method for material evaluation by acoustic velocity measurements, comprising the steps of:

(a) preparing a plurality of acoustical physical constants determining materials with different nominal chemical compositions;

(b) measuring one of the Curie temperature and lattice constant of each of said acoustical physical constant determining materials as a physical property, and calculating a true chemical composition D of said each acoustical physical constant determining material by use of a known relationship between said physical property and said chemical composition;

(c) preparing, from said each acoustical physical constant determining material, substrates for determining desired acoustical physical constants;

(d) measuring the acoustic velocities v ($v_{LSAW}$, $v_L$, $v_S$), dielectric constants and density for said acoustical physical constant determining substrates of different chemical compositions, and determining elastic and piezoelectric constants as acoustical physical constants of said each acoustical physical constant determining material based on measured values of said acoustic velocities, dielectric constants and density;

(e) measuring the acoustic velocities of a material to be evaluated, converting the measured values to desired parameters based on said acoustical physical constants, and evaluating said material based on said parameters; and (f) measuring the velocity of any one of a leaky surface acoustic wave, a surface acoustic wave, a longitudinal wave and a shear wave as said acoustic velocity; calibrating the scale of either one of said Curie temperature and said lattice constant by use of measured value of said acoustic velocity; and conducting material evaluation by use of either one of said calibrated Curie temperature and lattice constant.

15. The method of any one of claims 1, 2–4 or 9, wherein said material is a LiTaO$_3$ single crystal.

16. The method of any one of claims 1, 3–5 or 9, wherein said material is a LiNbO$_3$ single crystal.

* * * * *